United States Patent
Shi et al.

(10) Patent No.: US 12,410,425 B2
(45) Date of Patent: Sep. 9, 2025

(54) HIGHLY MULTIPLEXED PHYLOGENETIC IMAGING OF MICROBIAL COMMUNITIES

(71) Applicant: CORNELL UNIVERSITY, Ithaca, NY (US)

(72) Inventors: Hao Shi, Ithaca, NY (US); Iwijn De Vlaminck, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 1332 days.

(21) Appl. No.: 16/978,891

(22) PCT Filed: Mar. 7, 2019

(86) PCT No.: PCT/US2019/021088
§ 371 (c)(1),
(2) Date: Sep. 8, 2020

(87) PCT Pub. No.: WO2019/173555
PCT Pub. Date: Sep. 12, 2019

(65) Prior Publication Data
US 2021/0047634 A1    Feb. 18, 2021

Related U.S. Application Data

(60) Provisional application No. 62/640,239, filed on Mar. 8, 2018.

(51) Int. Cl.
| | |
|---|---|
| *C12N 15/10* | (2006.01) |
| *C12N 1/00* | (2006.01) |
| *C40B 20/00* | (2006.01) |
| *C40B 40/06* | (2006.01) |
| *G16B 25/00* | (2019.01) |

(52) U.S. Cl.
CPC ........... *C12N 15/1065* (2013.01); *C12N 1/00* (2013.01); *C40B 20/00* (2013.01); *C40B 40/06* (2013.01); *G16B 25/00* (2019.02)

(58) Field of Classification Search
CPC .. C12N 15/1065; C12N 1/00; C12N 15/1089; C40B 20/00; C40B 40/06; C40B 30/04; C40B 70/00; G16B 25/00; G16B 50/10; G16B 50/30; C12Q 1/02; G01N 33/533
See application file for complete search history.

(56) References Cited

U.S. PATENT DOCUMENTS

| | | | | |
|---|---|---|---|---|
| 4,716,106 A | * | 12/1987 | Chiswell ............... | C12Q 1/6876 435/6.15 |
| 2010/0323345 A1 | * | 12/2010 | Borisy ................. | C12Q 1/6841 435/6.12 |
| 2013/0274118 A1 | | 10/2013 | Curry | |
| 2017/0220733 A1 | * | 8/2017 | Zhuang ............... | C12Q 1/6844 |

FOREIGN PATENT DOCUMENTS

WO    WO-2016172643 A2 * 10/2016   ............. C40B 20/00

OTHER PUBLICATIONS

Wang MFZ. (Machine-) Learning to analyze in vivo microscope: support vector machines. BBA—Proteins and Proteomics 1865: 1719-1727. (Year: 2017).*
Daims H. Fluorescence in situ hybridization for the detection of prokaryotes. In Molecular Microbial Ecology, Taylor & Francis, 21 pgs. (Year: 2005).*
Buades A. et al., "Non-Local Means Denoising", Image Processing On Line 1:208-212 (2011).
Buades A. et al., "A Non-Local Algorithm for Image Denoising", 2005 IEEE Computer Society Conference on Computer Vision and Pattern Recognition (CVPR'05), p. 1-6, (2005).
Deweirdt R. et al., "Micromanagement in the Gut: Microenvironmental Factors Govern Colon Mucosal Biofilm Structure and Functionality", NPJ Biofilms and Microbiomes 1:15026 (2015), 6 pages.
Dewhirst F.E. et al., "The Human Oral Microbiome", Journal of Bacteriology 192(19):5002-5017 (Oct. 2010).
Donaldson G.P. et al., "Gut Biogeography of the Bacterial Microbiota", Nature 14:20-32 (Jan. 2016).
Earle K.A. et al., "Quantitative Imaging of Gut Microbiota Spatial Organization", Cell Host & Microbe 18:478-488 (2015).
Edgar R.C., "Search and Clustering Orders of Magnitude Faster Than BLAST", Bioinformatics 26(19):2460-2461 (2010).
Eng C-H L et al., "Transcriptome-Scale Super-Resolved Imaging in Tissues by RNA seqFISH+", Nature 568:235 (Apr. 11, 2019), 235-239.
Francino M.P., "Antibiotics and the Human Gut Microbiome: Dysbioses and Accumulation of Resistances", Frontiers In Microbiology 6(1543):1-10 (Jan. 2016).
Froment J., "Parameter-Free Fast Pixelwise Non-Local Means Denoising", Image Processing On Line 4:300-326 (2014).
Guizar-Sicairos M. et al., "Efficient Subpixel Image Registration Algorithms", Optics Letters 33(2):156-158 (Jan. 15, 2008).
Hedberg M.E. et al., "*Lachnoanaerobaculum* Gen. Nov., a New Genus in the Lachnospiraceae: Characterization of *Lachnoanaerobaculum umeaense* Gen. Nov., Sp. Nov., Isolated from the Human Small Intestine, and *Lachnoanaerobaculum orale* Sp. Nov., Isolated from Saliva, and Reclassification of Eubacterium Saburreum (Prevot 1966) Holdeman and Moore 1970 as *Lachnoanaerobaculum saburreum* Comb. Nov.", International Journal of Systematic and Evolutionary Microbiology 62:2685-2690 (2012).

(Continued)

*Primary Examiner* — Olivia M. Wise
*Assistant Examiner* — Robert J. Kallal
(74) *Attorney, Agent, or Firm* — Scully, Scott, Murphy & Presser, P.C.

(57) ABSTRACT

Micron scale biogeography is a major driver of physiology and ecology of complex microbial biofilm communities, which remains elusive largely due to the lack of tools for spatially resolved phylogenetic mapping. This disclosure provides methods, computer-readable storage devices and kits that allow highly multiplexed and spatially resolved imaging of microbial community spatial organization. The disclosure provides a highly-multiplexed approach to resolve the spatial structure of complex microbial community at high taxonomic resolution.

14 Claims, 20 Drawing Sheets
(17 of 20 Drawing Sheet(s) Filed in Color)
Specification includes a Sequence Listing.

(56) References Cited

OTHER PUBLICATIONS

Lehtinen J. et al., "Noise2Noise: Learning Image Restoration Without Clean Data", (available at http://arxiv.org/abs/1803.04189) (2018), 12 pages.
Manz W. et al., "Phylogenetic Oligodeoxynucleotide Probes for the Major Subclasses of Proteobacteria: Problems and Solutions", System Appln. Microbiol. 15:593-600 (1992).
Moffitt J.R. et al., "RNA Imaging With Multiplexed Error Robust Fluorescence In Situ Hybridization", Methods Enzymol. 572:1-49 (2016).
Otsu N., "A Threshold Selection Method from Gray-Level Histograms", IEEE Transactions on Systems, Man, and Cybernetics SMC-9(1):62-66 (Jan. 1979).
Sauvola J. et al., "Adaptive Document Image Binarization", Pattern Recognition 33:225-236 (2000).
Schlafer S. et al., "Filifactor Alocis-Involvement in Periodontal Biofilms", BMC Microbiology 10:66 (2010), 13 pages.
Shah S. et al., "seqFISH Accurately Detects Transcripts in Single Cells and Reveals Robust Spatial Organization in the Hippocampus", Neuron 94:752-758 (May 2017).
Shi H. et al., "Highly Multiplexed Spatial Mapping of Microbial Communities", bioRxiv, [online] [retrieved Jul. 2, 2019], Available on the Internet: <URL:https://www.biorxiv.org/content/10.1101/678672v1.full> Especially abstract (cited in ISR & Written Opinion), 29 pages.
Singer E. et al., "High-Resolution Phylogenetic Microbial Community Profiling", The ISME Journal 10:2020-2032 (2016).
Thaiss C.A. et al., "Microbiota Diurnal Rhythmicity Programs Host Transcriptome Oscillation", Cell 167:1495-1510 (Dec. 2016).
Tropini C. et al., "The Gut Microbiome: Connecting Spatial Organization to Function", Cell Host & Microbe 21:433-442 (Apr. 12, 2017).
Untergasser A. et al., "Primer3-New Capabilities and Interfaces", Nucleic Acids Research 40(15):e115 (Jun. 2012), 12 pages.
Valm A.M. et al., "Multiplexed Spectral Imaging of 120 Different Fluorescent Labels", :PLoS One, DOI: 10.1371/journal.pone.0158495 (Jul. 8, 2016), 17 pages.
Valm A.M. et al., "CLASI-FISH: Principles of Combinatorial Labeling and Spectral Imaging", Syst Appl Microbiol. 35 (8):496-502 (Dec. 2012).
Valm A.M. et al., "Systems-Level Analysis of Microbial Community Organization Through Combinatorial Labeling and Spectral Imaging", PNAS 108(10):4153-4157 (Mar. 8, 2011).
Weigert M. et al., "Content-Aware Image Restoration: Pushing the Limits of Fluorescence Microscopy", Nature Methods 15:1090-1097 (Dec. 2018).
Welch J.L. et al., "Spatial Organization of a Model 15-Member Human Gut Microbiota Established in Gnotobiotic Mice" PNAS E9105-E9114, doi:10.1073/pnas.1711596114 (Oct. 9, 2017).
Welch J.L. et al., "Biogeography of a Human Oral Microbiome at the Micron Scale", PNAS 13:E791-E800 (Jan. 25, 2016).
International Search Reprot and Written Opinion dated Jul. 29, 2019 received in International Application No. PCT/US19/21088.
Chen K H et al., "Spatially Resolved, Highly Multiplexed RNA Profiling in Single Cells", 348(6233):412 (Apr. 24, 2015).
Moffitt J.R. et al., "High-Performance Multiplexed Fluorescence In Situ Hybridization in Culture and Tissue With Matrix Imprinting and Clearing", PNAS 113(50):14456-14461 (Dec. 13, 2016).
Shi H. et al., "Recent Advances in Tools to Map the Microbiome", Current Opinion in Biomedical Engineering 19:100289 (2021).
Shi H. et al., "Highly Multiplexed Imaging of Microbial Diversity", APS March Meeting Abstracts, pp. 1-1 (Jan. 1, 2018).
European Extended Supplementary Search Report dated Jan. 25, 2022 received in European Application No. 19 76 3228.4.
European Communication dated Aug. 21, 2024 received in European Application No. 19 763 228.4.

* cited by examiner

A

B

A

B

SEQUENCE LISTING

```
<160> NUMBER OF SEQ ID NOS: 17

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide

<400> SEQUENCE: 1
tatccttcaa tccctccaca                                                20

<210> SEQ ID NO 2
<211> LENGTH: 20
<212> TYPE: DNA
<213> ORGANISM: Artificial Sequence
<220> FEATURE:
```

```
<223> OTHER INFORMATION: Oligonucleotide

<400> SEQUENCE: 2
acactaccac catttcctat                                                    20

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide

<400> SEQUENCE: 3
actccactac tactcactct                                                    20

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide

<400> SEQUENCE: 4
accctctaac ttccatcaca                                                    20

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide

<400> SEQUENCE: 5
accacaaccc attcctttca                                                    20

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide

<400> SEQUENCE: 6
tttactccct acacctccaa                                                    20

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide

<400> SEQUENCE: 7
accctttaca aacacaccct                                                    20

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide

<400> SEQUENCE: 8
tcctattctc aacctaacct                                                    20
```

```
<210> SEQ ID NO 9
<211> LENGTH: 20
<212> TYPE: DNA
<213> ORGANISM: Artificial Sequence
<220> FEATURE:
<223> OTHER INFORMATION: Oligonucleotide

<400> SEQUENCE: 9
ttctccctct atcaactcta                                              20

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide

<400> SEQUENCE: 10
acccttacta ctacatcatc                                              20

<210> SEQ ID NO 11
<211> LENGTH: 107
<212> TYPE: DNA
<213> ORGANISM: Artificial Sequence
<220> FEATURE:
<223> OTHER INFORMATION: Oligonucleotide

<400> SEQUENCE: 11
cgatgcgcca attccggttc tgtggaggga ttgaaggata aatctctcgc gagttcgcaa    60
ctcgaaccaa cccgcgagcg atgatcagtc tattttctta tccgacg               107

<210> SEQ ID NO 12
<211> LENGTH: 106
<212> TYPE: DNA
<213> ORGANISM: Artificial Sequence
<220> FEATURE:
<223> OTHER INFORMATION: Oligonucleotide

<400> SEQUENCE: 12
cgatgcgcca attccggttc ataggaaatg gtggtagtgt atggccgcgg gatcatccag    60
aagactcaac ccgcgagcga tgatcagtct attttcttat ccgacg                106

<210> SEQ ID NO 13
<211> LENGTH: 106
<212> TYPE: DNA
<213> ORGANISM: Artificial Sequence
<220> FEATURE:
<223> OTHER INFORMATION: Oligonucleotide

<400> SEQUENCE: 13
cgatgcgcca attccggttc ataggaaatg gtggtagtgt gagattcaac cgcgcgaagc    60
ccgttctgtg gagggattga aggatacaac ccgcgagcga tgatca               106

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide

<400> SEQUENCE: 14
agagtttgat cmtggctcag                                              20

<210> SEQ ID NO 15
```

```
<211> LENGTH: 22
<212> TYPE: DNA
<213> ORGANISM: Artificial Sequence
<220> FEATURE:
<223> OTHER INFORMATION: Oligonucleotide

<400> SEQUENCE: 15
tacggytacc ttgttacgac tt                                              22

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide

<400> SEQUENCE: 16
cgatgcgcca attccggttc                                                 20

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide

<400> SEQUENCE: 17
gtctattttc ttatccgacg                                                 20
```

HIGHLY MULTIPLEXED PHYLOGENETIC IMAGING OF MICROBIAL COMMUNITIES

CROSS REFERENCE TO RELATED APPLICATION

This application claims the benefit of priority from U.S. Provisional Application No. 62/640,239, filed Mar. 8, 2018, the contents of which are incorporated herein by reference.

STATEMENT REGARDING FEDERALLY SPONSORED RESEARCH OR DEVELOPMENT

This disclosure was made with government support under a research project supported by DP2 AI138242-01 awarded by the National Institutes of Health. The government has certain rights in this invention.

INCORPORATION BY REFERENCE OF SEQUENCE LISTING

The Sequence Listing in the ASCII text file, named as 35977_8158_03_US_Sequence_Listing.txt of 4 KB, created on Sep. 8, 2020, and submitted to the United States Patent and Trademark Office via EFS-Web, is incorporated herein by reference.

BACKGROUND

Bacteria can form biofilms, aggregations of microbial consortia, that are encased in a complex, self-produced polymeric matrix and that adhere to biological and non-biological surfaces. Environmental microbes frequently reside in biofilm microbial communities with rich taxonomic diversity and exquisite spatial organization. Biofilms have been observed on the intestinal mucosa of colorectal cancer patients, even on tumor-free mucosa far distant from the tumors. Patients with familial polypsis also harbor colonic biofilms that are comprised of tumorigenic bacteria.

The local environment of individual microbes can have strong influences on their physiology, which in turn shapes the ecology of the community. The oral plaque microbiome has been shown to exhibit intricate spatial structure, which is thought to contribute to the metabolic interactions within the microbial community, and between the community and the surrounding environment. In other instances, biofilm formation has been shown to lead to enhanced antimicrobial resistance and virulence.

Sequencing strategies have revealed extensive genomic information of microbial communities from a wide range of environments, ranging from human body sites to the global ocean, but at the expense of the spatial structure of these communities. In a typical metagenomic study, genomic material is generally extracted from biological samples for further molecular analysis. Imaging methods based on fluorescence in-situ hybridization (FISH) have enabled studies of the spatial organization of biofilms but suffers significant multiplexity limitations. Existing FISH strategies distinguish different taxa by conjugating each taxon-specific oligonucleotide probe with a unique fluorophore or a combination of fluorophores. The spectral overlap between commercially available fluorophores and the limited range of wavelength typically used in fluorescence imaging significantly limit the number of taxa that can be probed in a single experiment using current FISH-based strategies. Early reports with one fluorophore per taxa allow the identification of up to eight taxa per experiment. Subsequent improvements using a combination of two fluorophores per taxa enabled detection of up to 15 taxa with 6 fluorophores. Further improvements in image processing strategies have allowed detection of up to 120 differently labeled E. coli cells using 16 different fluorophores but has not been demonstrated in environmental microbial communities. The state-of-the-art method allows distinction of 15 taxa, which falls short of the diversity typically observed in natural biofilm communities.

In addition, quantitative measurements of spatial organization in microbial communities are limited by existing image segmentation algorithms. Single cell segmentation will allow physical measurements of cell size, cell shape, cell-to-cell distance, and cellular adjacency network. Previous reports have used various coarse-grained metrics to quantitatively dissect spatial organization of environmental microbial communities. However, microbes in environmental biofilms are typically densely packed, which reduces the contrast between intracellular space and cells. Furthermore, cells from different taxa typically contain different amounts of ribosome, leading to a high dynamic range of biofilm images. Both factors make single-cell segmentation challenging in images of environmental biofilms. There are existing tools that performs very well in adjusting images of uneven background. Even though these tools allow segmentation of objects with high dynamic range from the background, they often are not able to separate cells that are in close contact.

The FISH probes typically used in existing methods are limited in their taxonomic coverage. Due to the aforementioned multiplexity limit, most existing methods either (a) use probes for a limited number of taxa at low taxonomic levels (e.g., genus or species) or (b) use probes designed at high taxonomic levels (e.g., phylum or class). Using probes for a limited number of low level taxa risks missing many low-abundance taxa. On the other hand, high taxonomic level probes do not provide high phylogenetic resolution, and can suffer from incomplete coverage of species within the target taxon.

Microbes are a key component of the microenvironment of tumors that arise at epithelial barrier surfaces. In colorectal cancer (CRC), multiple lines of evidence point to a direct role for microbiota in tumor initiation and progression. The bacterium *Fusobacterium nucleatum* (Fn) has been identified as a CRC-promoting microbe that can i) affect tumor growth and inflammation, ii) inhibit T cell and NK cell immune responses, and iii) rewire tumors to resist chemotherapy. Fn and its associated microbiome, including myriad species of *Bacteroides, Selenomonas* and *Prevotella*, infiltrate and colonize CRCs. and persist in distal metastases. Both functional and organizational dysbiosis of the gut microbiome are hallmarks of CRC. Polymicrobial bacterial biofilm formation is associated with CRC and plays a role in disease progression by breaching the protective mucus layer that segregates microbiota from the colonic epithelium, thereby enabling direct host-microbiome interactions. Spatial interactions between microbes and between microbes and host tissues are fundamental to the mechanisms by which microbiota drive carcinogenesis in CRC, yet these interactions remain poorly studied. This lack of knowledge is in large part due to fundamental limitations of the tools available to study microbes and microbiomes. Microbiome studies primarily rely on shotgun DNA sequencing, which destroys all information about the spatial context of microbes and their functional interactions, or imaging methodologies that are limited to identifying a small number of organisms using general species marker tags.

The human oral microbiome harbors one of the most diverse microbial communities in the body. In addition to harboring phylogenetic complexity, the human oral microbial communities exhibit exquisite spatial organization at the micro-scale. The bacteria in these microbial communities are major players in common human oral cavity diseases, including dental caries and periodontal diseases. Multiple studies have suggested that disease state in the oral cavity is associated with altered oral microbiomes. The spatial relationship between different microbes and between microbes and the host tissue can play an important role in shaping the physiology and metabolism of the oral microbiome, which can influence the pathology of dental caries and periodontal diseases. However, current methodologies have not been able to study the spatial relationships between different microorganisms in the human oral microbiomes.

Since their introduction, *Caenorhabditis elegans* have played a large role in shaping our understanding of cell biology. However, *C. elegans* used for these studies are often fed on a simple diet of *E. coli*. Recent studies have revealed the complexity of the natural microbiome and its impact on *C. elegans* physiology. None of the current technologies can provide spatial and phylogenetic resolution of the *C. elegans* microbiome.

Planktonic microbial communities play a significant role in shaping the environment of our Earth. For example, the global ocean microbiome drives important transformations in the global elemental cycles. An accurate enumeration of individual bacterial taxa in the plankton is important to the understanding of their community ecology. Sequencing-based approaches have provided a great deal of insights into the composition of these communities, but they can often introduce amplification bias and drop-out bias due to the commonly used molecular biology workflow to generate sequencing libraries.

High throughout 16S and metagenomic sequencing has brought into spotlight the rich taxonomic diversity in naturally occurring microbial communities from a wide range of environments. However, sequencing strategy cannot resolve the spatial structure of these communities as sequencing library preparation requires the destruction of samples. Combinatorial fluorescence labeling approaches have revealed highly organized spatial structures in human oral microbial communities, but are limited by low multiplexity and suboptimal FISH probe design.

All bacteria have a unique 16S ribosomal RNA (16S rRNA) gene sequence that can serve as a tag for species identification and classification. Bacteria express 16S rRNA at high copy number (100s-1000s of copies).

BRIEF SUMMARY OF THE DISCLOSURE

In one aspect, the present disclosure is directed to a computer-readable storage device storing computer readable instructions for assigning each taxon in a list of taxa of microorganisms a unique n-bit binary code selected from a plurality of unique n-bit binary codes, wherein n is an integer greater than 1. In a specific embodiment, n is equal to or greater than 10 (e.g., 10, 11, 12, 13, 14, 15, 16, 17, 18, 19, 20, 21, 22, 23, 24, 25, 26, 27, 28, 29, 30 etc). In some embodiments, a list of taxa of microorganisms are provided, where each taxon in the list is assigned a unique n-bit binary code selected from a plurality of unique n-bit binary codes, where n is an integer greater than 1. In some embodiments, n is greater than or equal to 10 (e.g., 10, 11, 12, 13, 14, 15, 16, 17, 18, 19, 20, 21, 22, 23, 24, 25, 26, 27, 28, 29, 30 etc).

In some embodiments, the list of taxa of microorganisms is selected from a list of phyla, a list of classes, a list of orders, a list of families, a list of genera, or a list of species, of microorganisms. In some embodiments, the list of phyla of microorganisms include phyla Actinobacteria, Aquificae, Armatimonadetes, Bacteroidetes, Chlamydiae, Chlorobi, Chloroflexi, Chrysiogenetes, Cyanobacteria, Chrysiogenetes, Deferribacteres, Deinococcus-Thermus, Dictyoglomi, Elusimicrobia, Fibrobacteres, Firmicues, Fusobacteria, Gemmatimonadetes, Lentisphaerae, Nitrospirae, Planctomycetes, Proteobacteria, Spirochaetia, Synergistetes, Thermodesulfobacteria, Thermotogae, and Verrucomicrobia.

In some embodiments, the computer-readable storage device further comprises instructions for designing a set of decoding probes. In some embodiments, each decoding probe corresponds to a digit in the n-bit binary code, and is substantially complementary to a readout sequence selected from a set of n number of readout sequences. In some embodiments, each decoding probe comprises at least 10 nucleotides.

In some embodiments, the computer-readable storage device further comprises instructions for designing a set of encoding probes. In some embodiments, the set of encoding probes includes a plurality of subsets of encoding probes. In some embodiments, each encoding probe comprises a targeting sequence and one or more readout sequences. In some embodiments, the encoding probes within each subset comprise a targeting sequence that is specific to a taxon in the list of taxa of microorganisms and is different from a targeting sequence of the encoding probes of another subset. In some embodiments, the targeting sequence in the encoding probes of a subset is substantially complementary to a consensus 16S ribosomal sequence specific to a taxon. In some embodiments, the encoding probes within each subset comprise a plurality of targeting sequences, wherein the plurality of targeting sequences are specific to the same taxon.

In some embodiments, the readout sequences in the encoding probes within a subset are selected from the set of n number of readout sequences based on the unique n-bit binary code assigned to the taxon which the targeting sequence of the subset is specific to.

Another aspect of the disclosure is directed to a method of highly-multiplexed phylogenetic imaging of microbial communities. In some embodiments, the method comprises providing a list of taxa of microorganisms, where each taxon in the list is assigned a unique n-bit binary code selected from a plurality of unique n-bit binary codes. In some embodiments, n is an integer greater than 1. In some embodiments, n is an integer equal to or greater than 10 (e.g., 10, 11, 12, 13, 14, 15, 16, 17, 18, 19, 20, 21, 22, 23, 24, 25, 26, 27, 28, 29, 30 etc).

In some embodiments, the list of taxa of microorganisms is selected from a list of phyla, a list of classes, a list of orders, a list of families, a list of genera, or a list of species, of microorganisms. In some embodiments, the list of phyla of microorganisms include phyla Actinobacteria, Aquificae, Armatimonadetes, Bacteroidetes, Chlamydiae, Chlorobi, Chloroflexi, Chrysiogenetes, Cyanobacteria, Chrysiogenetes Deferriacteres, Deinococcus-Thermus, Dictyoglomi, Elusimicrobia, Fibrobacteres, Firmicutes, Fusobacteria, Gemmatimonadetes, Lentisphaerae, Nitrospirae, Planctomycetes, Proteobacteria, Spirochaetia, Synergistetes, Thermodesulfobacteria, Thermotogae, and Verrucomicrobia.

In some embodiments, the method further comprises providing a set of n number of decoding probes. In some embodiments, each decoding probe corresponds to a digit in the plurality of unique n-bit binary codes. In some embodiments, each decoding probe comprises at least 10 nucleotides. In some embodiments, each decoding probe is conjugated with a label that provides a detectable signal. In some embodiments, the labels on the decoding probes are different from each other. In some embodiments, the label is a fluorophore. In some embodiments, the label is a fluorophore that has an emission wavelength in the near-infrared region of the electromagnetic spectrum. In some embodiments, the fluorophore selected from the group consisting of Alexa 405, Pacific Blue, Pacific Green, Alexa 488, Alexa 532, Alexa 546, Rhodamine Red X, Alexa 610, Alexa 647, DyLight-510-LS, Hydroxycoumarin, methoxycoumarin, Cy2, FAM, Flourescein FITC, Alexa 430, R-phycoerythrin (PE), Tamara, Cy3.5 581, Rox, Alexa fluor 568, Red 613, Texas Red, Alexa fluor 594. Alexa fluor 633. Alexa fluor 660, Alexa fluor 680, Cy5, Cy 5.5, Cy 7, and Allophycocyanin. In some embodiments, each decoding probe is substantially complementary to a readout sequence selected from a set of n number of readout sequences.

In some embodiments, the method further comprises providing a set of encoding probes. In some embodiments, each encoding probe comprises a targeting sequence and one or more readout sequences. In some embodiments, each encoding probe comprises a 3-nucleotide spacer between the targeting sequence and the one or more readout sequences.

In some embodiments, the set of encoding probes includes a plurality of subsets of encoding probes. In some embodiments, the encoding probes within each subset comprise a targeting sequence that is specific to a taxon in the list of taxa of microorganisms. In some embodiments, the targeting sequence for a subset of encoding probes is substantially complementary to a consensus 16S ribosomal sequence specific to a taxon. In some embodiments, each targeting sequence comprises at least 15 nucleotides. In some embodiments, the encoding probes within each subset are different from a targeting sequence of the encoding probes of another subset. In some embodiments, the encoding probes within each subset comprise a plurality of targeting sequences, wherein the encoding probes within each subset comprise a plurality of targeting sequences, wherein the plurality of targeting sequences are specific to the same taxon. In some embodiments, the readout sequences in the encoding probes within a subset are selected from the set of n number of readout sequences based on the unique n-bit binary code assigned to the taxon which the targeting sequence of the subset is specific to.

In some embodiments, the method further comprises providing a sample suspected of comprising one or more of the taxa of microorganisms. In some embodiments, the method further comprises contacting the sample with the set of encoding probes to permit hybridization of the targeting sequences to the corresponding taxa of microorganisms present in the sample. In some embodiments, the method further comprises subsequently contacting the sample with the set of decoding probes to permit hybridization of one or more decoding probes to the readout sequences in encoding probes that are bound to the sample. In some embodiments, the sample is washed after each hybridization.

In some embodiments, the method further comprises detecting the decoding probes that are bound to the sample, and determining the unique binary codes based on the detected decoding probes. In some embodiments, the detecting is achieved by a microscope. In a specific embodiment, the microscope is a confocal microscope. In a specific embodiment, the microscope is a fluorescence microscope.

In some embodiments, the determining is achieved by a support vector machine. In some embodiments, the method further comprises identifying the taxa of microorganisms present in the sample based on the determined unique binary codes.

In some embodiments, the sample is selected from an environmental sample, and a biological sample. In some embodiments, the biological sample is selected from the group consisting of bronchoalveolar lavage fluid (BAL), blood, serum, plasma, urine, cerebrospinal fluid, pleural fluid, synovial fluid, peritoneal fluid, amniotic fluid, gastric fluid, lymph fluid, interstitial fluid, tissue homogenate, cell extracts, saliva, sputum, stool, physiological secretions, tears, mucus, sweat, milk, semen, seminal fluid, and vaginal secretions. In some embodiments, the sample is a solid sample or a liquid sample.

Yet another aspect of the disclosure is directed to a kit comprising components to be used for a method of highly-multiplexed phylogenetic imaging of microbial communities. In some embodiments, the kit comprises a list of taxa of microorganisms, wherein each taxon is assigned a unique n-bit binary code selected from a plurality of unique n-bit binary codes, wherein n is an integer greater than 1. In some embodiments, n is an integer equal to or greater than 10 (e.g., 10, 11, 12, 13, 14, 15, 16, 17, 18, 19, 20, 21, 22, 23, 24, 25, 26, 27, 28, 29, 30 etc).

In some embodiments, the list of taxa of microorganisms is selected from a list of phyla, a list of classes, a list of orders, a list of families, a list of genera, or a list of species, of microorganisms. In some embodiments, the list of phyla of microorganisms include phyla Actinobacteria, Aquificae, Armatimonadetes, Bacteroidetes, Chlamydiae, Chlorobi, Chloroflexi, Chrysiogenetes, Cyanobacteria, Chrysiogenetes, Deferribacteres, Deinococcus-Thermus, Dictyogloni, Elusimicrobia, Fibrobacteres, Firmicutes, Fusobacteria, Gemmatimonadetes, Lentisphaerae, Nitrospirae Planctomycetes, Proteobacteria, Spirochaetia, Synergistetes, Thermodesulfobacteria, Thermotogae, and Verrucomicrobia.

In some embodiments, the kit further comprises a set of n number of decoding probes. In some embodiments, each decoding probe corresponds to a digit in the plurality of unique n-bit binary codes. In some embodiments, each decoding probe comprises at least 10 nucleotides. In some embodiments, each decoding probe is conjugated with a label that provides a detectable signal. In some embodiments, the labels on the decoding probes are different from each other. In some embodiments, the label is a fluorophore. In some embodiments, the label is a fluorophore that has an emission wavelength in the near-infrared region of the electromagnetic spectrum. In some embodiments, the fluorophore selected from the group consisting of Alexa 405, Pacific Blue, Pacific Green, Alexa 488, Alexa 532, Alexa 546, Rhodamine Red X, Alexa 610, Alexa 647, DyLight-510-LS, Hydroxycoumarin, methoxycoumarin, Cy2, FAM, Flourescein FITC, Alexa 430, R-phycoerythrin (PE), Tamara, Cy3.5 581, Rox, Alexa fluor 568, Red 613, Texas Red, Alexa fluor 594, Alexa fluor 633, Alexa fluor 660, Alexa fluor 680, Cy5, Cy 5.5, Cy 7, and Allophycocyanin. In some embodiments, each decoding probe is substantially complementary to a readout sequence selected from a set of n number of readout sequences.

In some embodiments, the kit further comprises instructions on how to design a set of encoding probes. In some embodiments, the set of encoding probes includes a plurality of subsets of encoding probes. In some embodiments, the encoding probes within each subset comprise a targeting sequence that is specific to a taxon in the list of taxa of microorganisms. In some embodiments, the targeting sequence for a subset of encoding probes is substantially complementary to a consensus 16S ribosomal sequence specific to a taxon. In some embodiments, each targeting sequence comprises at least 15 nucleotides. In some embodiments, the encoding probes within each subset are different from a targeting sequence of the encoding probes of another subset. In some embodiments, the encoding probes within each subset comprise a plurality of targeting sequences, wherein the encoding probes within each subset comprise a plurality of targeting sequences, wherein the plurality of targeting sequences are specific to the same taxon. In some embodiments, the readout sequences in the encoding probes within a subset are selected from the set of n number of readout sequences based on the unique n-bit binary code assigned to the taxon which the targeting sequence of the subset is specific to.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE DISCLOSURE

General Description

Figure 1A:
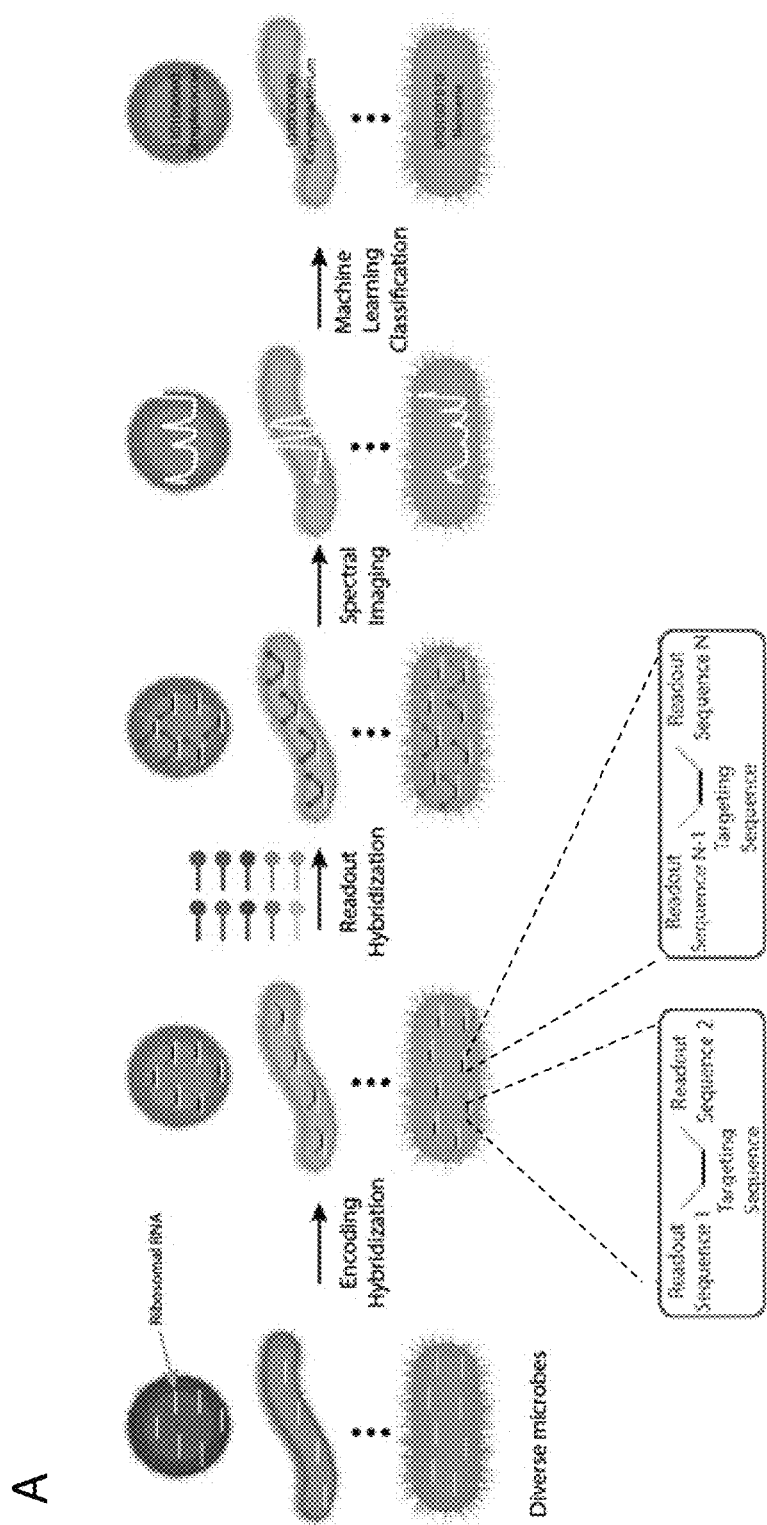
FIGS. 1A-1D. (A) The concept of High Phylogenetic Resolution Fluorescence In-situ Hybridization (HiPR-FISH) takes advantage of the high abundance of ribosomes in microbial cells to label a given species of bacteria with up to 10 kinds of fluorophores, enabling 1023-plex multiplexity. (B) Scheme to identify different microbial species with different 16S ribosomal rRNA gene sequences. Each species is tagged with a 10-bit digital code and the binary sequence I registered using spectral imaging. Spectral imaging of ten fluorophores enables identification of >1000 unique species of differently labeled *E. coli* cells. (C) Example single cell spectrum acquired using spectral imaging. Images of cells are first segmented using a custom imaging processing algorithm. For each single cell, a spectrum is measured by averaging intensity values over all pixels belong to that cell. (D) A UMAP representation of all 1023 experimentally measured spectra using a 10-bit system.

The present disclosure is directed to a novel approach to label individual species as n-bit binary combinations of fluorophores, where n is the number of unique fluorophores. Also known as, High Phylogenetic Resolution Fluorescence In-situ Hybridization (HiPR-FISH), the methods described herein start with n-bit binary numbers assigned to individual taxon, where each bit corresponds to a unique fluorophore. Each taxon-specific oligonucleotide probe designed using a custom bioinformatics pipeline is then conjugated to appropriate flanking encoding sequences according to the binary number assignment. During a two-step hybridization, the bacterial cells are first hybridized with taxon-specific FISH probes conjugated with appropriate encoding sequences, and then hybridized with a panel of readout probes, each complementary to one of the encoding sequences and conjugated to a unique fluorophore. Following hybridization, the emission profile of each bacterial cell is read out by spectral imaging, allowing individual cells to be assigned to their corresponding taxa.

In some embodiments, the present disclosure is directed to a method that achieves high phylogenetic resolution by taking advantage of the abundance of existing 16S ribosomal RNA sequence information and a highly multiplexed binary encoding scheme. In some embodiments, each taxon from a list of taxa of microorganisms is probed with a custom designed taxon-specific targeting sequence, flanked by a subset of n unique encoding sequences. In some embodiments, each taxon is assigned a unique n-bit binary word, where 1 or 0 at the $i^{th}$ bit indicates the taxon-specific targeting sequence is flanked or not flanked by the $i^{th}$ encoding sequence. In some embodiments, a mixture of n decoding probes, each complementary to one of the n encoding sequences and conjugated to a unique label, is allowed to hybridize to their complementary encoding sequences. In some embodiments, the spectrum of labels for each cell is then detected using spectral imaging techniques. In some embodiments, the barcode identity for each cell can then be assigned using a support vector machine, using spectra of cells encoded with known barcodes as training data.

Sample

In some embodiments, the sample used in the present disclosure is a solid or a liquid.

In some embodiments, the sample is an environmental sample, or a microbial biofilm on a surface. In some embodiments, the sample is an environmental sample comprising planktonic microbial communities.

Assays, for example as described in the Examples below, may be carried out using methods of the disclosure in a biological sample, e.g., a biological fluid or a tissue sample. In some embodiments, the biological sample includes, without limitation, bronchoalveolar lavage fluid (BAL), blood, serum, plasma, urine, cerebrospinal fluid, pleural fluid, synovial fluid, peritoneal fluid, amniotic fluid, gastric fluid, lymph fluid, interstitial fluid, tissue homogenate, cell extracts, saliva, sputum, stool, physiological secretions, tears, mucus, sweat, milk, semen, seminal fluid, vaginal secretions, fluid from ulcers and other surface eruptions, blisters, and abscesses, and extracts of tissues including biopsies of normal, malignant, and suspect tissues or any other constituents of the body which may contain the target particle of interest. Other similar specimens such as cell or tissue culture or culture broth are also of interest.

In a specific embodiment, the sample is from a patient suffering from, or suspected to suffer from, colorectal cancer (CRC).

In some embodiments, the sample is a human oral microbiome sample.

In some embodiments, the sample is a whole organism. In a specific embodiment, the organism is *C. elegans*.

Taxa of Microorganisms

As used herein a "taxon" refers to a group of one or more populations of an organism or organisms. In some embodiments, a "taxon" refers to a phylum, a class, an order, a family, a genus or a species. In some embodiments, the disclosure comprises providing a list of taxa of microorganisms. In some embodiments, the list of taxa of microorganisms is selected from a list of phyla, a list of classes, a list of orders, a list of families, a list of genera, or a list of species, of microorganisms.

In some embodiments, the list of phyla of microorganisms include phyla Actinobacteria, Aquificae, Armatimonadetes, Bacteroidetes, Chlamydiae, Chlorobi, Chloroflexi, Chrysiogenetes, Cyanobacteria, Chrysiogenetes, Deferribacteres, Deinococcus-Thermus, Dictyoglomi, Elusimicrobia, Fibrobacteres, Firmicutes, Fusobacteria, Gemmatimonadetes, Lentisphaerae, Nitrospirae, Planctomycetes, Proteobacteria, Spirochaetia, Synergistetes, Thermodesulfobacteria, Thermotogae, and Verrucomicrobia.

n-Bit Binary Encoding

In some embodiments, each taxon from a list of taxa of microorganisms is assigned a unique n-bit binary code selected from a plurality of unique n-bit binary codes, where n is an integer greater than 1.

A "binary code" refers to a representation of taxa using a string made up of a plurality of "0" and "1" from the binary number system. The binary code is made up of a pattern of n binary digits (n-bits), where n is an integer representing the number of labels used. The bigger the number n, the greater number of taxa can be represented using the binary code. For example, a binary code of eight bits (an 8-bit binary code, using 8 different labels) can represent up to 255 ($2^8-1$) possible taxa. (One is subtracted from the total possible number of codes because no taxon is assigned a code of all zeros "00000000." A code of all zeros would mean no decoding sequence, and thus no label, is attached. In other words, there are no non-labeled taxa.) Similarly, a binary code of ten bits (a 10-bit binary code) can represent up to 1023 ($2^{10}-1$) possible taxa. In some embodiments a binary code may be translated into and represented by a decimal number. For example, the 10-bit binary code "0001100001" can also be represented as the decimal number "97."

Each digit in a unique binary code represents whether a readout probe and the fluorophore corresponding to that readout probe are present for the selected species. In some embodiments, each digit in the binary code corresponds to a Readout probe (from Readout probe 1 (R1) through Readout probe n (Rn) in an n-bit coding scheme). In a specific embodiment, the n is 10 and the digits of an n-bit code correspond to R1 through R10 as shown in FIG. 1F. In some embodiments, the fluorophores that correspond to R1 through Rn are determined arbitrarily. In a specific embodiment, n is 10, and R1 corresponds to an Alexa 488 fluorophore, R2 corresponds to an Alexa 546 fluorophore, R3 corresponds to a 6-ROX (6-Carboxy-X-Rhodamine, or Rhodamine Red X) fluorophore, R4 corresponds to a PacificGreen fluorophore, R5 corresponds to a PacificBlue fluorophore. R6 corresponds to an Alexa 610 fluorophore, R7 corresponds to an Alexa 647 fluorophore, R8 corresponds to a DyLight-510-LS fluorophore, R9 corresponds to an Alexa 405 fluorophore, and R10 corresponds to an Alex532 fluorophore. In some embodiments, other fluorophores including, but not limited to Hydroxycoumarin, methoxycoumarn, Cy2, FAM, Flourescein FITC, Alexa 430, R-phycoerythrin (PE), Tamara, Cy3.5 581, Rox, Alexa fluor 568, Red 613, Texas Red, Alexa fluor 594, Alexa fluor 633, Alexa fluor 660. Alexa fluor 680, Cy5, Cy 5.5, Cy 7, and Allophycocyanin are used in the n-bit encoding system.

In some embodiments, the n-bit binary code is selected from the group consisting of 2-bit binary code, 3-bit binary code, 4-bit binary code, 5-bit binary code, 6-bit binary code, 7-bit binary code, 8-bit binary code, 9-bit binary code, 10-bit binary code, 11-bit binary code, 12-bit binary code, 13-bit binary code, 14-bit binary code, 15-bit binary code, 16-bit binary code, 17-bit binary code, 18-bit binary code, 19-bit binary code, 20-bit binary code, 21-bit binary code, 22-bit binary code, 23-bit binary code, 24-bit binary code, 25-bit binary code, 26-bit binary code, 27-bit binary code, 28 bit binary code, 29-bit binary code, and 30-bit binary code.

Encoding Probes

In some embodiments, 16S rRNA gene is used as a marker for phylogenetic placement. In some embodiments, methods of the present disclosure comprise multiplexed in-situ hybridization of encoding probes targeting taxon-specific segments of multiple unique 16S rRNA genes present in a microorganism population.

In some embodiments, a set of encoding probes comprises subsets of encoding probes, wherein each subset targets a specific taxon. In some embodiments, a subset of encoding probes contains one unique targeting sequence specific to a taxon; that is, the encoding probes within a subset share a common targeting sequence specific to a taxon. In some embodiments, a subset of encoding probes contains multiple unique targeting sequences, each unique targeting sequence being specific to the same taxon as other targeting sequences within the same subset.

Targeting Sequences

In some embodiments, each encoding probe comprises a targeting sequence which is substantially complementary to a taxon-specific 16S rRNA sequence. By "substantially complementary" it is meant that the nucleic acid fragment is capable of hybridizing to at least one nucleic acid strand or duplex even if less than all nucleobases do not base pair with a counterpart nucleobase. In certain embodiments, a "substantially complementary" nucleic acid contains at least one sequence in which about 70%, about 71%, about 72%, about 73%, about 74%, about 75%, about 76%, about 77%, about 77%, 8%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range therein, of the nucleobase sequence is capable of base-pairing with at least one single or double stranded nucleic acid molecule during hybridization.

In some embodiments, the targeting sequence is designed to have a predicted melting temperature of between about 55° C. and about 65° C. As used herein, the term "about" refers to an approximately ±10% variation from a given value. In some embodiments, the predicted melting temperature of the targeting sequence is 55° C., 56° C., 57° C. 58° C., 59° C., 60° C. 61° C., 62° C., 63° C., 64° C. or 65° C. In some embodiments, the targeting sequence has a GC content of about 55%, 60%, 65% or 70%.

In some embodiments, the taxon-specific targeting sequence in an encoding probe is designed as follows. At first, 16S sequences from a plurality of microorganisms are grouped by taxon and sequence similarity and a consensus sequence is generated for each taxon. In a specific embodiment, the consensus sequence is generated using usearch and probes for each consensus sequence are designed. In some embodiments, a targeting sequence specific for a consensus sequence is at least 15 nucleotides long, at least 16 nucleotides long, at least 17 nucleotides long, at least 18 nucleotides long, at least 19 nucleotides long, at least 20 nucleotides long, at least 21 nucleotides long, at least 22 nucleotides long, at least 23 nucleotides long, at least 24 nucleotides long, at least 25 nucleotides long, at least 26 nucleotides long, at least 27 nucleotides long, at least 28 nucleotides long, at least 29 nucleotides long, at least 30 nucleotides long, at least 35 nucleotides long, at least 40 nucleotides long, at least 45 nucleotides long, or at least 50 nucleotides long. In some embodiments, the candidate targeting sequence is aligned against a catalogue of all full-length 16S rRNA sequences of a list of microorganisms. In a specific embodiment, the alignment is performed using Blastn (NCBI). In some embodiments, a maximum continuous homology (MCH) score, defined as the maximum number of continuous bases that are shared between the query and the target sequence, is calculated for each blast hit. In some embodiments, only candidate targeting sequences having blast hits to the consensus sequence above a threshold MCH score are considered significant and used for further analysis. In some embodiments, a blast on-target rate, defined as the ratio between the number of correct blast hits and the total number of significant blast hits, is calculated for each candidate targeting sequence having a significant blast hit. In some embodiments, any candidate targeting sequence with a blast on-target rate of less than 1 is excluded from the probe set to avoid ambiguity, and the remaining candidate targeting sequences are used as targeting sequences in encoding probe synthesis.

In some embodiments, the targeting sequence of an encoding probe is designed using publicly-available 16S rRNA sequence data. In some embodiments, the targeting sequence of an encoding probe design is designed using custom catalogues of 16S rRNA sequences. In a specific embodiment, high-quality, full-length 16S sequences are obtained by circular consensus sequencing (SMRT-CCS).

In some embodiments, SMRT-CCS of a 16S ribosomal sequence involves isolating ribosomal DNA from a microorganism. In a specific embodiment, DNA isolation is achieved using QIAamp DNA Mini Kit. In some embodiments, ribosomal DNA amplified using universal primers. In a specific embodiment, the universal primers are 27F (AGAGTTTGATCMTGGCTCAG (SEQ ID NO: 14)) and 1492R (TACGGYTACCTTGTTACGACTT (SEQ ID NO: 15)). In some embodiments, the amplified ribosomal DNA is purified, and sequenced. In a specific embodiment, sequencing is performed on a PacBio Sequel instrument. In some embodiments, sequence data is processed to create a circular consensus sequence with a threshold of 99% accuracy. In a specific embodiment, the sequence data processing is achieved using rDnaTools. In some embodiments, the circular consensus sequences are used for probe design. In some embodiments, to increase the sequence design space, and to improve identification of closely related species, the workflow uses a full 16S-23S rRNA region.

In some embodiments, the targeting sequence of an encoding probe is designed using a database that is relevant for a system. In a specific embodiment, the system is the gut microbiome. In some embodiments, the targeting sequence of an encoding probe is designed using a database that is relevant for a disease. In a specific embodiment, the disease is inflammatory bowel disease. In a specific embodiment, the disease is colorectal cancer.

Spacers

Figure 5:
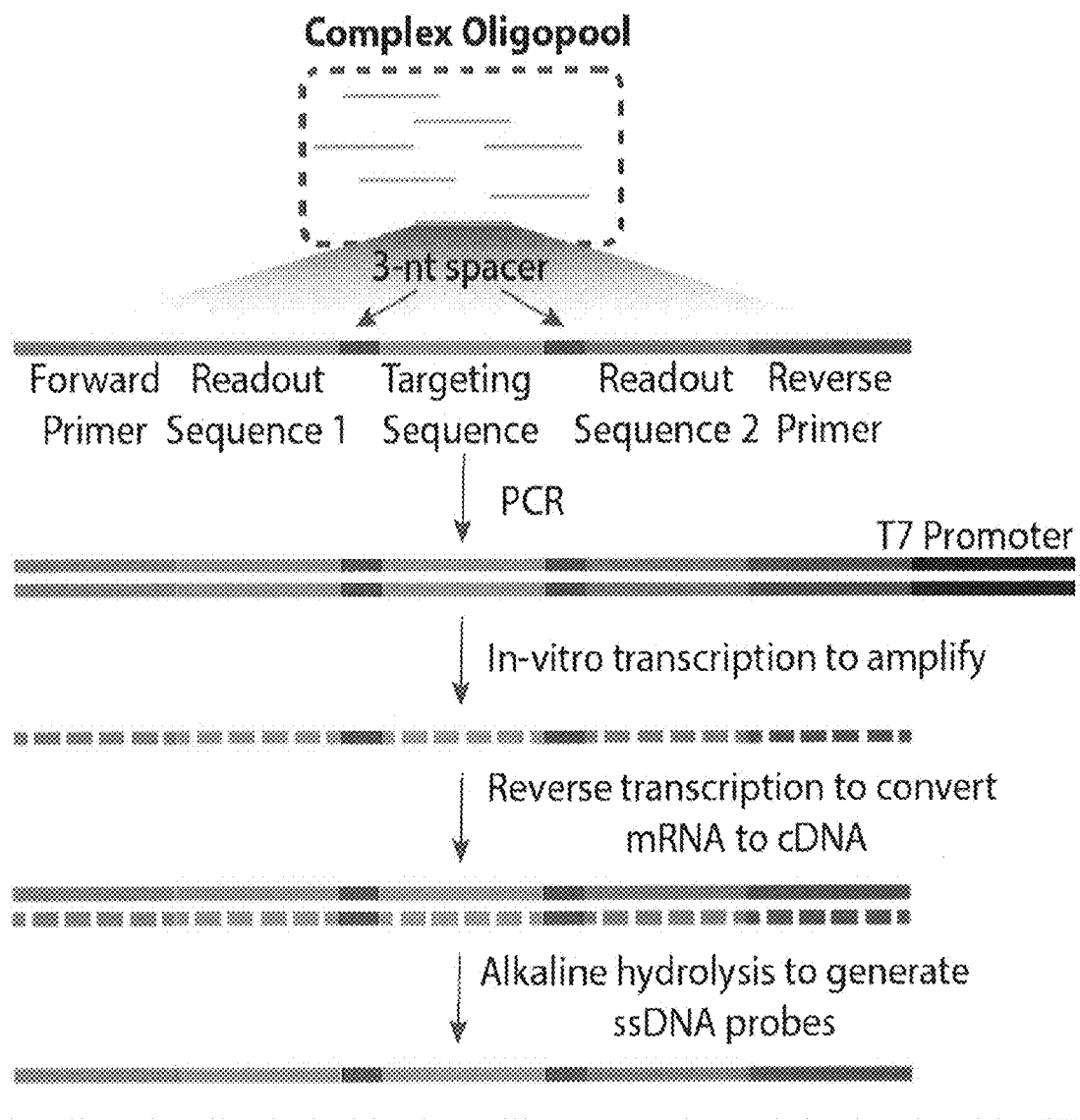
FIG. 5. Workflow for the synthesis of a complex pool of encoding probes.

In some embodiments, a targeting sequence in an encoding probe is concatenated on both ends with 3 nucleotide (3-nt) spacers. In some embodiments, the spacers are positioned as shown in FIG. 5. In some embodiments, the 3-nt spacers comprise a random string of three nucleotides. In some embodiments, the 3-nt spacers are sequences designed from the 16S rRNA molecule (i.e., three nucleotides upstream and downstream of the selected 16S targeting sequence is used as the 3-nt spacers).

Readout Sequences

In some embodiments, a targeting sequence is concatenated to at least one readout sequence depending on the unique n-bit binary code assigned to the taxon that the targeting sequence is specific for. Each readout sequence is substantially complementary to the sequence of a corresponding labeled readout probe.

In some embodiments, a readout sequence is at least 15 nucleotides long, at least 16 nucleotides long, at least 17 nucleotides long, at least 18 nucleotides long, at least 19 nucleotides long, at least 20 nucleotides long, at least 21 nucleotides long, at least 22 nucleotides long, at least 23 nucleotides long, at least 24 nucleotides long, at least 25 nucleotides long, at least 26 nucleotides long, at least 27 nucleotides long, at least 28 nucleotides long, at least 29 nucleotides long, or at least 30 nucleotides long.

In some embodiments, candidate readout sequences are blasted against a nucleotide database to ensure that they are not substantially complementary to regions of 16S ribosomal sequences.

Forward and Reverse Primers

In some embodiments, a targeting sequence is concatenated to a set of sequences (forward primer and reverse primer sequences) that are substantially complementary to primers that can be used to amplify the encoding probe in a polymerase chain reaction (PCR). In some embodiments, the forward and reverse primers are designed to have predicted melting temperatures of between about 55° C. and about 65° C. As used herein, the term "about" refers to an approximately ±10% variation from a given value. In some embodiments, the predicted melting temperature of the forward and reverse primers are 55° C., 56° C., 57° C., 58° C., 59° C., 60° C., 61° C., 62° C., 63° C., 64° C. or 65° C. In some embodiments, the forward and reverse primers have a GC content of about 55%, 60%, 65% or 70%.

In some embodiments, the set of forward and reverse primers are designed such that the set of forward and reverse primers are not substantially complementary to the targeting sequence or readout sequences. In some embodiments, the set of forward and reverse primers are designed such that the set of forward and reverse primers are not substantially complementary to any sequences that are substantially complementary to the targeting sequence or readout sequences. In a specific embodiment, the set of forward primer and reverse primer sequences comprise the nucleotide sequence CGATGCGCCAATTCCGGTTC (SEQ ID NO: 16) and the nucleotide sequence GTCTATITTCT-TATCCGACG (SEQ ID NO: 17).

In some embodiments, the forward primer or the reverse primer is at least 15 nucleotides long, at least 16 nucleotides long, at least 17 nucleotides long, at least 18 nucleotides long, at least 19 nucleotides long, at least 20 nucleotides long, at least 21 nucleotides long, at least 22 nucleotides long, at least 23 nucleotides long, at least 24 nucleotides long, at least 25 nucleotides long, at least 26 nucleotides long, at least 27 nucleotides long, at least 28 nucleotides long, at least 29 nucleotides long, or at least 30 nucleotides long.

Decoding Probes

In some embodiments, the present disclosure utilizes a set of n number of decoding probes representing an n-bit coding scheme where n is an integer. In some embodiments, each probe in the set of decoding probes corresponds to a digit in the plurality of unique n-bit binary codes.

In some embodiments, each probe in the set of decoding probes is conjugated with a label that provides a detectable signal.

In some embodiments, each probe in a set of decoding probes is labeled different from other probes in the set, and each decoding probe is substantially complementary to a corresponding readout sequence selected from a set of n number of readout sequences;

In a specific embodiment, the detectable signal is a fluorophore. In some embodiments, the detectable signal is a fluorophore that emits light in infrared or near-infrared. In a specific embodiment, the fluorophore is selected from the group consisting of Alexa 405, Pacific Blue, Pacific Green, Alexa 488, Alexa 532, Alexa 546, Rhodamine Red X. Alexa 610, Alexa 647, and DyLight-510-LS, Hydroxycoumarin, methoxycoumarin, Cy2, FAM, Flourescein FITC, Alexa 430, R-phycoerythrin (PE). Tamara, Cy3.5 581, Rox, Alexa fluor 568, Red 613, Texas Red. Alexa fluor 594, Alexa fluor 633, Alexa fluor 660, Alexa fluor 680, Cy5, Cy 5.5, Cy 7, and Allophycocyanin.

In some embodiments, a readout probe is at least 10 nucleotides long, at least 11 nucleotides long, at least 12 nucleotides long, at least 13 nucleotides long, at least 14 nucleotides long, at least 15 nucleotides long, at least 16 nucleotides long, at least 17 nucleotides long, at least 18 nucleotides long, at least 19 nucleotides long, at least 20 nucleotides long, at least 21 nucleotides long, at least 22 nucleotides long, at least 23 nucleotides long, at least 24 nucleotides long, at least 25 nucleotides long, at least 26 nucleotides long, at least 27 nucleotides long, at least 28 nucleotides long, at least 29 nucleotides long, or at least 30 nucleotides long.

In a specific embodiment, the n-bit binary code is a 10-bit binary code and the readout probes R1 through R10 are selected from the sequences SEQ ID NOs: 1 through 10. In a specific embodiment, the readout probes R1 through R10 are labeled as shown in Table 2.

Imaging

In some embodiments, the labels used in the present methods are imaged using a microscope. In some embodiments, the microscope is a confocal microscope. In some embodiments, the microscope is a fluorescence microscope.

Barcode Decoding

In some embodiments, a support vector machine is trained on reference data to predict the barcode of single cells in the synthetic communities and environmental samples. In a specific embodiment, the support vector machine is SVR, sklearn.svm from Python package. As used herein, the term "support-vector machine" (SVM) refers to a supervised learning model with associated learning algorithms that analyze data used for classification and regression analysis. Given a set of training examples, each marked as belonging to one or the other of two categories, an SVM training algorithm builds a model that assigns new examples to one category or the other, making it a non-probabilistic binary linear classifier. An SVM model is a representation of the examples as points in space, mapped so that the examples of the separate categories are divided by a clear gap that is as wide as possible. New examples are then mapped into that same space and predicted to belong to a category based on which side of the gap they fall.

In some embodiments, the reference spectra are obtained through a brute force approach involving the measurement of the spectra of all possible barcodes using barcoded test *E. coli* cells. In some embodiments, the n-bit binary encoding is a 10-bit binary encoding and the reference spectra are obtained through measuring 1023 reference spectra.

In some embodiments the reference spectra are obtained by simulation of all possible spectra. In some embodiments, the simulated spectral data can be used as reference examples for the support vector machine. In some embodiments, the spectra corresponding to individual n-bit binary codes are simulated by adding together the measured spectra of each individual fluorophore (e.g., the reference spectrum for 0000010011 is generated by adding the spectra of R1, R2, and R5; or the reference spectrum for 1010010100 is generated by adding the spectra of R3, R5, R8 and R10).

Studying Tumor-Microbiome Relationships

In some embodiments, the methods of the present disclosure are used to study tumor-microbiome relationships in human cancers. In a specific embodiment, the human cancer is colorectal cancer (CRC).

In some embodiments, the disclosure enables comparisons of microbial community architectures in tissue proximal and distal to colonic adenomas and carcinomas and determinations of the extents to which surrounding tissues are altered in CRC. In some embodiments, the instant methods are used to build an atlas of tumor-infiltrating microbiota, and examine whether microbiota that colonize colonic tumors also colonize metastases. In some embodiments, the present methods are used to evaluate host transcriptional responses to mucosa and tumor-infiltrating bacteria and examine the microbial interactions that underlie colon cancer carcinogenesis.

Dental Caries and Periodontal Diseases

In some embodiments, the methods of the present disclosure are to generate spatial maps of human oral microbiomes with high phylogenetic and spatial resolution. In some embodiments, the spatial maps of human oral microbiomes provide insights into the disease initiation, progression, and outcome of these common human oral diseases.

*Caenorhabditis elegans* Microbiome

In some embodiments, the methods of the present disclosure are used to complement existing sequencing strategies and map out the spatial structure of the natural microbiome of *C. elegans*. In some embodiments, the spatial maps can provide useful insights into host-microbe interaction and the impact of the natural microbiome on *C. elegans* physiology.

Microbial Ecology of Plankton

In some embodiments, the present disclosure provides a high-throughput imaging-based alternative to enumerate different bacterial taxa with high accuracy. In some embodiment, the present imaging methods are performed together with DAPI staining. In some embodiments, when the present methods are combined with a DAPI stain, fraction of the community that are missed can be estimated.

Computer-Readable Storage Devices

In one aspect, the disclosure is directed to a computer-readable storage device storing computer readable instructions, which when executed by a processor causes the processor to assign each taxon in a list of taxa of microorganisms a unique n-bit binary code selected from a plurality of unique n-bit binary codes, and design decoding and encoding probes suitable for use in such n-bit binary coding scheme.

The phrase "computer-readable storage device" refers to a computer readable storage device or a computer readable signal medium. A computer-readable storage device, may be, for example, a magnetic, optical, electronic, electromagnetic, infrared, or semiconductor system, apparatus, or device, or any suitable combination of the foregoing; however, the computer readable storage device is not limited to these examples except a computer readable storage device excludes computer readable signal medium. Additional examples of the computer readable storage device can include: a portable computer diskette, a hard disk, a magnetic storage device, a portable compact disc read-only memory (CD-ROM), a random access memory (RAM), a read-only memory (ROM), an erasable programmable read-only memory (EPROM or Flash memory), an optical storage device, or any appropriate combination of the foregoing: however, the computer readable storage device is also not limited to these examples. Any tangible medium that can contain, or store, a program for use by or in connection with an instruction execution system, apparatus, or device could be a computer readable storage device.

A computer readable signal medium may include a propagated data signal with computer readable program code embodied therein, such as, but not limited to, in baseband or as part of a carrier wave. A propagated signal may take any of a plurality of forms, including, but not limited to, electromagnetic, optical, or any suitable combination thereof. A computer readable signal medium may be any computer readable medium (exclusive of computer readable storage device) that can communicate, propagate, or transport a program for use by or in connection with a system, apparatus, or device. Program code embodied on a computer readable signal medium may be transmitted using any appropriate medium, including but not limited to wireless, wired, optical fiber cable, RF, etc., or any suitable combination of the foregoing.

The term "memory" as used herein comprises program memory and working memory. The program memory may have one or more programs or software modules. The working memory stores data or information used by the CPU in executing the functionality described herein.

The term "processor" may include a single core processor, a multi-core processor, multiple processors located in a single device, or multiple processors in wired or wireless communication with each other and distributed over a network of devices, the Internet, or the cloud. Accordingly, as used herein, functions, features or instructions performed or configured to be performed by a "processor", may include the performance of the functions, features or instructions by a single core processor, may include performance of the functions, features or instructions collectively or collaboratively by multiple cores of a multi-core processor, or may include performance of the functions, features or instructions collectively or collaboratively by multiple processors, where each processor or core is not required to perform every function, feature or instruction individually. The processor may be a CPU (central processing unit). The processor may comprise other types of processors such as a GPU (graphical processing unit). In other aspects of the disclosure, instead of or in addition to a CPU executing instructions that are programmed in the program memory, the processor may be an ASIC (application-specific integrated circuit), analog circuit or other functional logic, such as a FPGA (field-programmable gate array), PAL (Phase Alternating Line) or PLA (programmable logic array).

The CPU is configured to execute programs (also described herein as modules or instructions) stored in a program memory to perform the functionality described herein. The memory may be, but not limited to, RAM (random access memory), ROM (read-only memory) and persistent storage. The memory is any piece of hardware that is capable of storing information, such as, for example without limitation, data, programs, instructions, program code, and/or other suitable information, either on a temporary basis and/or a permanent basis.

In some embodiments, a computer-readable storage device comprises instructions for assigning each taxon in a list of taxa of microorganisms a unique n-bit binary code selected from a plurality of unique n-bit binary codes; designing a set of n number of decoding probes, wherein each decoding probe corresponds to a digit in the n-bit binary code, and where each decoding probe is substantially complementary to a readout sequence selected from a set of n number of readout sequences, and designing a set of encoding probes, where the set of encoding probes includes a plurality of subsets of encoding probes, wherein each encoding probe comprises a targeting sequence and one or more readout sequences, the encoding probes within each subset comprise a targeting sequence that is specific to a taxon in the list of taxa of microorganisms and is different from a targeting sequence of the encoding probes of another subset, and the readout sequences in the encoding probes within a subset are selected from the set of n number of readout sequences based on the unique n-bit binary code assigned to the taxon which the targeting sequence of the subset is specific to.

In some embodiments, the computer-readable storage device comprises instructions for designing encoding probes of a subset, wherein the targeting sequence in the encoding probes of a subset is substantially complementary to a consensus 16S ribosomal sequence specific to a taxon. In some embodiments, the targeting sequence is blasted against a nucleotide database to ensure that the target sequence is not substantially complementary to any sequence other than the consensus 16S ribosomal sequence to which the target sequence is specific.

In some embodiments, a set of encoding probes comprises subsets of encoding probes, wherein each subset targets a specific taxon. In some embodiments, a subset of encoding probes contains one unique targeting sequence specific to a taxon; that is, the encoding probes within a subset share a common targeting sequence specific to a taxon. In some embodiments, a subset of encoding probes contains multiple unique targeting sequences, each unique targeting sequence being specific to the same taxon as other targeting sequences within the same subset.

Figures 11A, 11B:
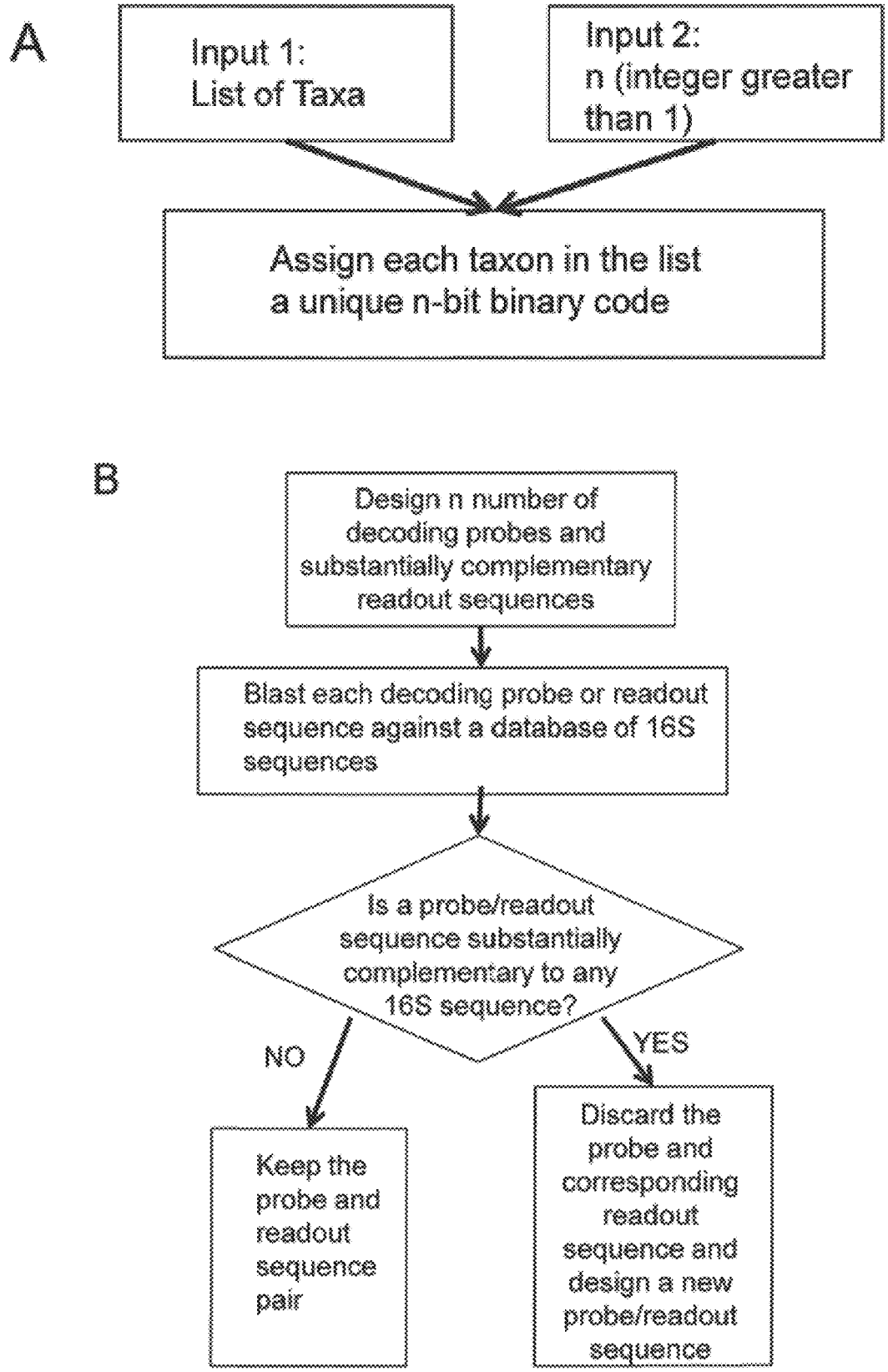
FIGS. 11A-11C. Flowcharts of non-limiting examples in accordance with aspects of the disclosure. (A) Flowchart of an example of assigning unique n-bit codes to each taxon in a list of taxa (B) Flowchart of an example of designing decoding probes. (C) Flowchart of an example of designing encoding probes. The features and orders of the features shown in the flowcharts can be modified by the skilled artisan.
Figure 11C:
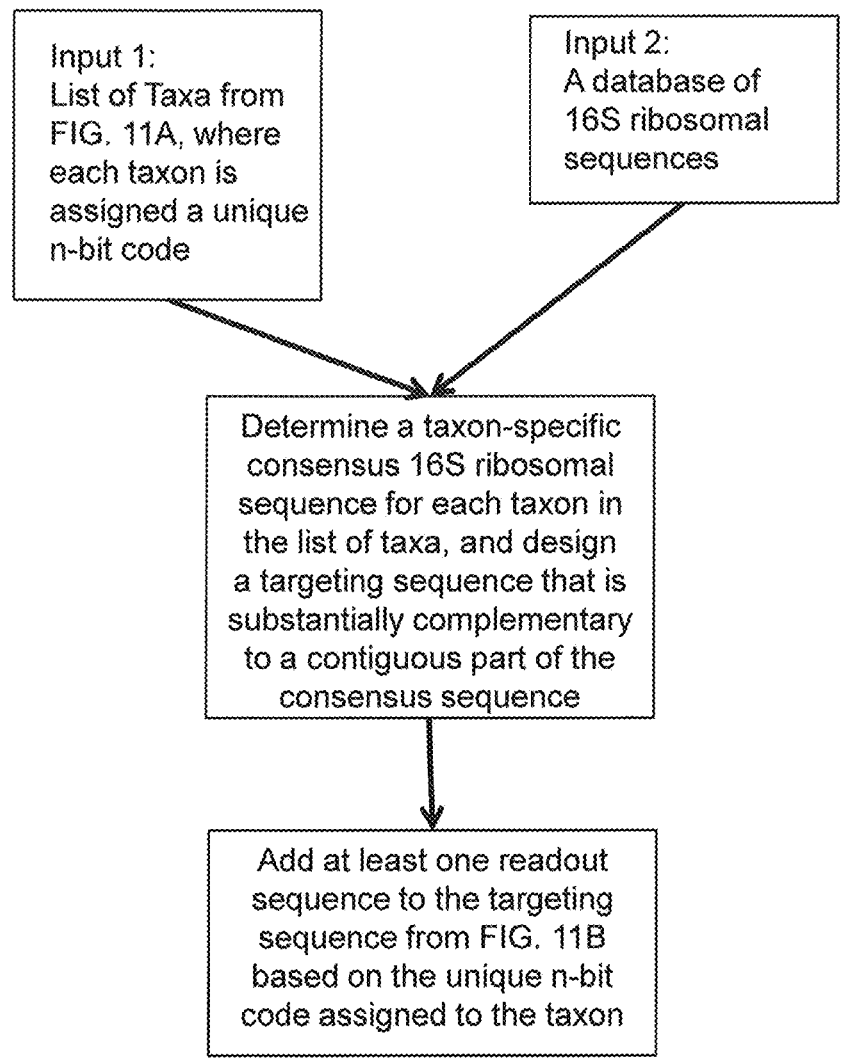

In a specific embodiment, the computer-readable storage device comprises instructions to follow the features shown in FIGS. 11A-11C.

Kits

Another aspect of the disclosure is directed to kits that allow practicing the methods of the present disclosure.

In some embodiments, the disclosure is directed to a kit which includes a list of taxa of microorganisms, wherein each taxon is assigned a unique n-bit binary code selected from a plurality of unique n-bit binary codes, wherein n is an integer greater than 1; a set of n number of decoding probes, wherein each decoding probe corresponds to a digit in the plurality of unique n-bit binary codes, is conjugated with a label that provides a detectable signal, wherein the labels on the decoding probes are different from each other, and is substantially complementary to a readout sequence selected from a set of n number of readout sequences; and instructions on how to design a set of encoding probes, wherein the set of encoding probes includes a plurality of subsets of encoding probes, wherein each encoding probe comprises a targeting sequence and one or more readout sequences, the encoding probes within each subset comprise a targeting sequence that is specific to a taxon in the list of taxa of microorganisms and is different from a targeting sequence of the encoding probes of another subset, and the readout sequences in the encoding probes within a subset are selected from the set of n number of readout sequences based on the unique n-bit binary code assigned to the taxon which the targeting sequence of the subset is specific to.

In some embodiments, the encoding probes within each subset comprise at least one targeting sequence that is specific to a taxon. In some embodiments, the encoding probes within each subset comprise at least two targeting sequences that are specific to the same taxon.

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The present disclosure is further illustrated by the following non-limiting examples.

EXAMPLES

Example 1: Materials and Methods

Cell Culture

All cultured cells were inoculated from frozen stock stored at −80° C. into 4 mL of appropriate growth medium. A loopful of the liquid culture was streaked on an appropriate agar plate. A single colony from the agar plate was finally inoculated into appropriate liquid medium and grown to roughly mid-exponential phase. Details of growth media and growth time is listed in Table 1.

TABLE 1

Information for species used in the synthetic community experiment.

| Species | Gram | Med. | Temp. | $1^{st}$ liq. Gr. | Plate | $2^{nd}$ liq. Gr. |
|---|---|---|---|---|---|---|
| Escherichia coli MG1655 | − | LB | 37° C. | O/N | O/N | 16 hrs |
| Acetobacter Tropicalis | − | MRS | 30° C. | O/N | O/N | 16 hrs |
| Acetobacter Pomorum | − | MRS | 30° C. | O/N | O/N | 16 hrs |
| Lactobacillus Brevis | + | MRS | 30° C. | O/N | O/N | 16 hrs |
| Lactobacillus Pomorum | + | MRS | 30° C. | O/N | O/N | 16 hrs |

TABLE 1-continued

Information for species used in the synthetic community experiment.

| Species | Gram | Med. | Temp. | 1st liq. Gr. | Plate | 2nd liq. Gr. |
|---|---|---|---|---|---|---|
| Vibrio albensis | − | LB | 37° C. | O/N | O/N | 16 hrs |
| C. glutamicum | + | TGY | 30° C. | O/N | O/N | 16 hrs |
| Acinetobacter schindleri | − | TGY | 37° C. | O/N | O/N | 16 hrs |
| Comamonas Testosteroni | − | LB | 30° C. | O/N | O/N | 16 hrs |
| Enterococcus gallinarum | + | MRS | 37° C. | O/N | O/N | 16 hrs |
| Xanthomonas vasicola | − | TGY | 30° C. | O/N | O/N | 16 hrs |

Gram: gram staining result (positive (+), or negative (−)); Med.: Growth medium; Temp.: Growth temperature; 1st liq. Gr.: first liquid growth period; 2nd liq. Gr.: second liquid growth period; O/N: overnight.

PacBio Sequencing

Metagenomic DNA from plaque samples were extracted using the QIAamp DNA Mini Kit according to manufacturer's protocol. Ribosomal DNA was amplified from the extracted metagenomic DNA using the universal primers for the 16S rRNA (27F (AGAGTTTGATCMTGGCTCAG (SEQ ID NO: 14)) and 1492R (TACGGYTACCTTGTTACGACTT (SEQ ID NO: 15)), cleaned with the MinElute PCR purification Kit according to manufacturer's protocol, and sequenced on aPacBio RSII or Sequel at the Duke Center for Genomic and Computational Biology. The PacBio sequence data was processed using the rDnaTools (Github) package, with a threshold of 99% accuracy. The output FASTA sequences of the rDnaTools pipeline was used for probe design.

Probe Design and Synthesis

The 16S rRNA sequences for cultured were downloaded from NCBI GenBank, and those for environmental samples were generated via PacBio sequencing. Probes were designed using a custom pipeline (the custom pipeline comprising usearch (Drive 5 Bioinformatics Software), Primer3, and Blastn (NCBI)) in Python. Briefly, the 16S sequences were grouped by taxon and sequence similarity. A consensus sequence was generated for each taxon using usearch. FISH probes for each consensus sequence were designed using Primer3. The probes were then blasted against the database containing all 16S sequences from the community using Blastn. A maximum continuous homology (MCH) score was calculated for each blast hit. The "MCH score" refers to the maximum number of continuous bases that are shared between the query and the target sequence. Only blast hits above a threshold MCH score are considered significant and used for further analysis. The blast on-target rate and taxonomic coverage were calculated for each significant blast hit. "Blast on-target rate" refers to the ratio between the number of correct blast hits and the total number of significant blast hits. The phrase "taxonomic coverage" refers to the ratio between the number of significant blast hits within the target species and the total number of sequences for the target species. Any probe with a blast on-target rate of less than 1 is excluded from the probe set to avoid ambiguity. For each taxon, the probe with the highest taxonomic coverage is then selected to be part of the final probe set. Each probe is then concatenated on both ends with 3-nt spacers, readout sequences, and primer sequences. The 3-nt spacers for each probe are taken from the three bases upstream and downstream from the target region on the 16S sequence of the probe. The probes for the synthetic community experiment were purchased from Integrated DNA Technologies (IDT). The probes for the human plaque experiment were purchased as a single complex oligo pool from CustomArrays. The complex oligo pool was synthesized. Briefly, the complex oligo pool was PCR amplified to incorporate T7 promoters, in vitro transcribed, reverse transcribed, and purified using ethanol precipitation.

Synthesis of Complex Oligo Pools Comprising Encoding Probes

Because the encoding probes are not conjugated to fluorophores, they can be synthesized electrochemically, on arrays of electrodes. DNA synthesis using array technology is relatively inexpensive, for example a complex pool of 12,472 different oligos of length 80-109 bp can be designed.

To create single-stranded DNA oligo probes from this complex pool (FIG. 5), the pool is first PCR amplified to incorporate T7 promoters. In vitro translation is then used to uniformly amplify the pool. Next, reverse transcription PCR is used to create RNA/DNA hybrid copies of the RNA pool. Finally, single-stranded DNA copies of the oligo pool are created by alkaline hydrolysis of the RNA strands in the RNA/DNA hybrids.

Fluorescent Readout Probes

Fluorophore conjugated readout probes were purchased from Integrated DNA Technologies and Biosynthesis. The sequences of the readout probes are listed in Table 2.

TABLE 2

Readout probe sequences and corresponding labels.

| Probe | 5' Label | Sequence | 3' Label | SEQ ID NO |
|---|---|---|---|---|
| 1 | Alexa 488 | TATCCTTCAATCCCTCCACA | N/A | SEQ ID NO: 1 |
| 2 | Alexa 546 | ACACTACCACCATTTCCTAT | N/A | SEQ ID NO: 2 |
| 3 | 6-ROX | ACTCCACTACTACTCACTCT | 6-ROX | SEQ ID NO: 3 |
| 4 | Pacific Green | ACCCTCTAACTTCCATCACA | N/A | SEQ ID NO: 4 |
| 5 | Pacific Green | ACCACAACCCATTCCTTTCA | N/A | SEQ ID NO: 5 |
| 6 | Alexa 610 | TTTACTCCCTACACCTCCAA | N/A | SEQ ID NO: 6 |

TABLE 2-continued

Readout probe sequences and corresponding labels.

| Probe | 5' Label | Sequence | 3' Label | SEQ ID NO |
|---|---|---|---|---|
| 7 | Alexa 647 | ACCCTTTACAAACACACCCT | N/A | SEQ ID NO: 7 |
| 8 | DyLight-510-LS | TCCTATTCTCAACCTAACCT | DyLight-510-LS | SEQ ID NO: 8 |
| 9 | Alexa 405 | TTCTCCCTCTATCAACTCTA | N/A | SEQ ID NO: 9 |
| 10 | Alexa 532 | ACCCTTACTACTACATCATC | Alexa 532 | SEQ ID NO: 10 |

HIPR-FISH on Synthetic *E. coli* Communities

*E. coli* cells were grown overnight on LB agar plate. A single colony from the plate was inoculated into 800 mL of LB broth supplemented with 40 mL of 1M potassium phosphate buffer and 40 mL of 20% glucose solution. Cells were grown for 7 hours to an OD of 1.1. Cultured cells were fixed for 1.5 hours by addition of 800 mL of 2% freshly made formaldehyde. Fixed cells were aliquoted into 50 mL tubes, concentrated by centrifugation at 4000 RPM for 15 minutes, resuspended in of IX PBS (1 mL per tube), and pooled together into 2 50 mL tubes (~16 mL of *E. coli* suspension each). The cell suspensions were washed 3 times in 1× Phosphate-Buffered Saline (PBS) (50 mL per wash per tube), suspended in 50% ethanol, and stored at −20° C. until use Before the encoding hybridization experiment, the cell suspension was treated with lysozyme solution (10 mg/mL in 10 mM Tris-HCl, pH 8) for 30 minutes, washed once with 1×PBS, and resuspended in 50% EtOH. Every 9.9 mL of encoding hybridization buffer includes 4 mL of cell suspension (in 50% EtOH) resuspended in 5.8 mL of Ultrapure water, 1 mL of 20×SSC, 1 mL of Denhardt's solution, 2 mL of ethylene carbonate, and 100 µL of 1% SDS. Encoding hybridization buffers were aliquoted into 1.5 mL Eppendorf tubes at 99 µL per tube Finally, 1 µL of the encoding probe for a barcode was added to each tube. The encoding hybridization suspension was briefly vortexed, incubated at 46° C. for 4 hours, washed once in Washing Buffer (215 mM NaCl, 20 mM Tris, pH 7.5, and 5 mM EDTA) for 15 minutes at 48° C., washed twice in PBS, and resuspended in 100 µL of 50% EtOH. The 1023-plex synthetic community of barcoded *E. coli* was generated by mixing together 1 µL of each barcoded *E. coli* stock. To generate the titration community, the 1023 barcodes were randomly divided into 8 groups (7 communities with 128 barcodes each, and one community with 127 barcodes). Each 128-plex or 127-plex titration community were generated by mixing together a variable amount of barcoded *E. coli* stock. All synthetic community mixes were resuspended in 100 µL of 50% EtOH.

HiPR-FISH on Synthetic Multi-Species Microbial Communities

Cultured cells were fixed by adding an equal volume of 2% freshly made formaldehyde to the liquid culture for 1.5 hours. Fixed cells were washed 3 times in 1×PBS, permeated in absolute ethanol for 15 minutes, suspended in 50% ethanol, and stored at −20° C. until use. For each species control experiment, 1 µl of pure culture was deposited onto a UltraStick slide and air dried. To permeate cell walls, 20 µL of 10 mg/ml lysozyme suspended in 10 mM Tris-HCl was deposited onto the slide in a Frame-Seal in-situ hybridization chamber and incubated it at 37° C. for 0.5 hours. After lysozyme incubation, the slides were washed in IX PBS for 15 minutes, dipped in pure ethanol, briefly rinsed with pure ethanol to chase away any residual PBS, and air dried. The encoding hybridizations were performed in a 9×9 mm Frame-Seal hybridization chambers with 18 µl encoding hybridization buffer per slide at 46° C. for 2 hours. The slides were then washed in the Washing Buffer (215 mM NaCl, 20 mM Tris. pH 7.5, and 5 mM EDTA) at 48° C. for 15 minutes, dipped in room temperature pure ethanol, rinsed with pure ethanol, and air dried Readout hybridizations were carried out at 46° C. for 1 hour. The slides were washed and dried as described above and embedded in 15 µl Prolong Gold Anti-fade embedding medium. For the synthetic community experiment, all bacterial suspensions were mixed together at equal volume, and 1 µL of the mixture was deposited onto an UltraStick slide and air dried. Lysozyme digestion, encoding, and readout hybridization were carried out as described above.

HIPR-FISH on Human Oral Biofilm Samples.

Human plaque biofilm sample were obtained from a volunteer who refrained from oral hygiene for 24-48 hours. Subgingival plaque was collected using a stainless-steel dental pick, gently deposited into 1 mL of 50% ethanol, and stored at 4° C. until use. For each human plaque experiment, 20 µL of plaque material was deposited onto an UltraStick slide and air dried. The slides were then fixed in 2% freshly made formaldehyde for 1.5 hours, washed in IX PBS for 15 minutes, dipped in pure ethanol, rinsed with pure ethanol, and air dried. Lysozyme digestion, encoding, and readout hybridizations are carried out as described above.

HIPR-FISH on Mouse Tissue

Mouse were ordered from Jackson Laboratories, co-housed for 14 days, and subjected to antibiotics treatments. Mouse were sacrificed 7- or 8-days post antibiotics treatment using $CO_2$ asphyxiation. The entire digestive track posterior to the stomach is fixed in Carnoy's solution (60% ethanol, 30% chloroform, and 10% glacial acetic acid) for 48 hours at room temperature. Fixed tissues were rinsed three times in ethanol and stored in 70% ethanol at −20° C. until paraffin embedding and sectioning. Tissues were embedded in paraffin and sectioned to 5 µm thickness following standard tissue processing protocol at Cornell Vet School. Tissue sections on glass slides were incubated at 60° C. for 10 minutes, washed once in xylene substitute for 10 minutes, once in xylene substitute at room temperature for 10 minutes, once in ethanol at room temperature for 5 minutes, and air dried. To reduce autofluorescence, deparaffinized slides were washed with 1% sodium borohydride in phosphate buffer saline on ice for 30 minutes, with buffer change every 10 minutes, followed by three washes in 1×PBS on ice for 5 minutes each. Slides were briefly dipped in ethanol and allowed to air dry. Lysozyme digestion, encoding, and readout hybridization are carried out as described above.

Spectral Imaging

Spectral images were recorded on an inverted Zeiss 880 confocal microscope equipped with a 32-anode spectral detector, a Plan-Apochromat 63X/1.40 Oil objective, and excitation lasers at 405 nm, 488 nm, 514 nm, 561 nm, and 633 nm. The image acquisition settings are listed in Table 3 and Table 4.

TABLE 3

Laser settings for HiPR-FISH imaging.

| Setting | Excitation | Laser Power | Master Gain | Emission Range | Emission Channel Width | # of Emission Channels |
|---|---|---|---|---|---|---|
| hiprfish_405 | 405 nm | 2.00% | 800 | 410 nm-695 nm | 8.9 nm | 32 |
| hiprfish_488 | 488 nm | 1.50% | 800 | 491 nm-695 nm | 8.9 nm | 23 |
| hiprfish_514 | 514 nm | 6.00% | 800 | 517 nm-695 nm | 8.9 nm | 20 |
| hiprfish_561 | 561 nm | 0.40% | 800 | 517 nm-695 nm | 8.9 nm | 14 |
| hiprfish_633 | 633 nm | 1.50% | 800 | 642 nm-695 nm | 8.9 nm | 6 |

TABLE 4

Microscope settings for HiPR-FISH imaging.

| Setting | Pixel Time | Scan Mode | Scan Direction | Beam Splitter | Averaging | Bit Depth |
|---|---|---|---|---|---|---|
| hiprfish_405 | 2.11 μs | LineSequential | UniDirectional | MBS 405 | 4 | 8 |
| hiprfish_488 | 1.06 μs | LineSequential | UniDirectional | MBS 488 | 4 | 8 |
| hiprfish_514 | 1.06 μs | LineSequential | UniDirectional | MBS 458/514 | 4 | 8 |
| hiprfish_561 | 1.06 μs | LineSequential | UniDirectional | MBS 488/561 | 4 | 8 |
| hiprfish_633 | 1.06 μs | LineSequential | UniDirectional | MBS 488/561/633 | 4 | 8 |

The image pixel size was 70×70 nm to ensure sampling at the Nyquist frequency (defined as half of the sampling rate of a discrete signal processing system. Nyquist frequency is sometimes known as the folding frequency of a sampling system). The field of view size was 2000×2000 pixel, corresponding to a physical size of 135×135 μm. z-stacks were obtained with voxel size 70×70×150 nm to ensure sampling at the Nyquist frequency. For each pixel in the field of view, images were collected at five excitation wavelengths, and concatenated to form a 95-channel image. The emission spectra of each fluorophore were clearly distinct. Examples of fluorophores that have been used are illustrated in FIGS. 7A-7D.

Flat Field Correction

To correct for the non-uniformity of the optical system across the field of view, we imaged a uniformly fluorescent flat field correction slide. One microliter of each readout probe was added to 90 μl of ProLong Glass embedding medium. The solution was vortexed and briefly centrifuged. Finally, 15 μL of the mixture was deposited onto a UltraStick slide, and a1 1.5 coverslip was gently placed on top of the embedding medium. The flat field correction slide cured in the dark overnight and was imaged using the acquisition settings in Table 4. Two fields of view of the flat field correction slide were averaged to generate the flat field correction image.

Measurement of Point Spread Function

The point spread function for the microscope was measured using a total of 10 beads.

Reference Spectra Measurement

The reference spectrum for each binary word is measured using E. coli cells encoded with the corresponding barcode. For each barcode, one can usually measure about $c_i \approx 300$-500 single cell spectra in a single field of view.

Reference Spectra Training

For each barcode, the average and standard deviation of the spectra were first calculate, which were then used to simulate 5000 synthetic spectra Cultured Cell Imaging For each field of view, images were collected at five excitation wavelengths, and concatenated to form a 95-channel image. The pixel size is 70 nm×70 nm to ensure sampling at the Nyquist frequency. Each field of view is 2000-pixel×2000-pixel, corresponding to a physical size of 135 μm×135 μm.

Biofilm Imaging

Figure 8:
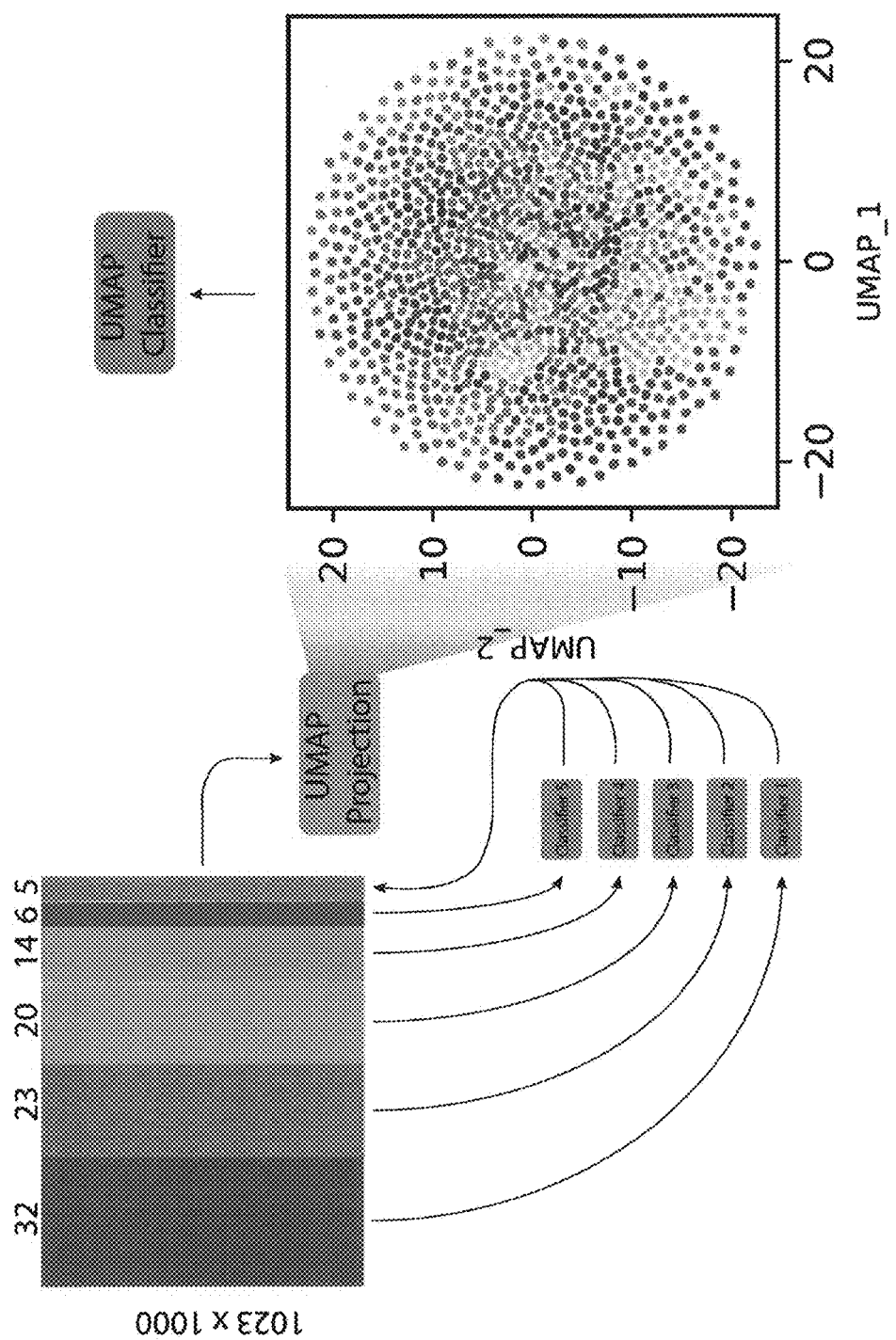
FIG. 8. Spectra classification algorithm using Uniform Manifold Approximation and Projection (UMAP) and support vector machine classifiers. For spectra acquired with each laser, a support vector machine was train to decide whether the detected spectra are signal or background. The five-column matrix indicating the presence or absence of signal in spectra acquired with each laser is concatenated with the spectra and sent to a UMAP transform with a custom defined metric. The custom defined metric is defined as the average cosine distance between two spectra acquired using the same laser. A final support vector machine is trained on the two-dimensional UMAP projection of the high-dimensional spectral data.
Figure 9A:
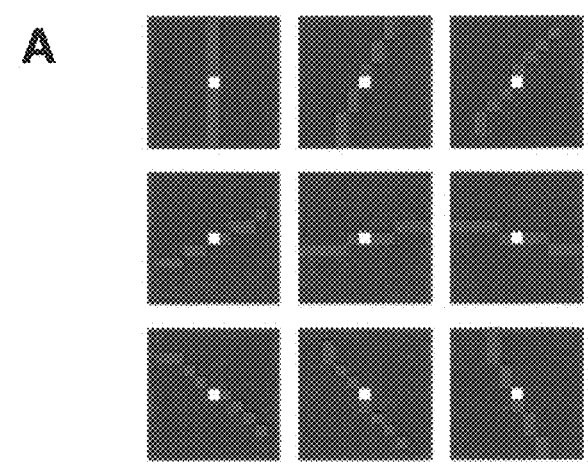
FIGS. 9A-9B. (A) An example 2D line profile structuring element used in the custom image processing algorithm. (B) Local neighborhood enhancement using intensity profiles along different directions in the vicinity of a given pixel. Extracted line intensity profiles were column-wise normalized. The average and coefficient of variation of the value of the pixel in the column-wise normalized matrix was used to calculate the enhanced pixel intensity. The enhanced image is then segmented using the watershed algorithm as implemented in scikit-image. Scikit-image, as used herein, refers to an open-source image processing library for the Python programming language. The scikit-image library includes algorithms for segmentation, geometric transformations, color space manipulation, analysis, filtering, morphology, and feature detection.
Figure 9B:
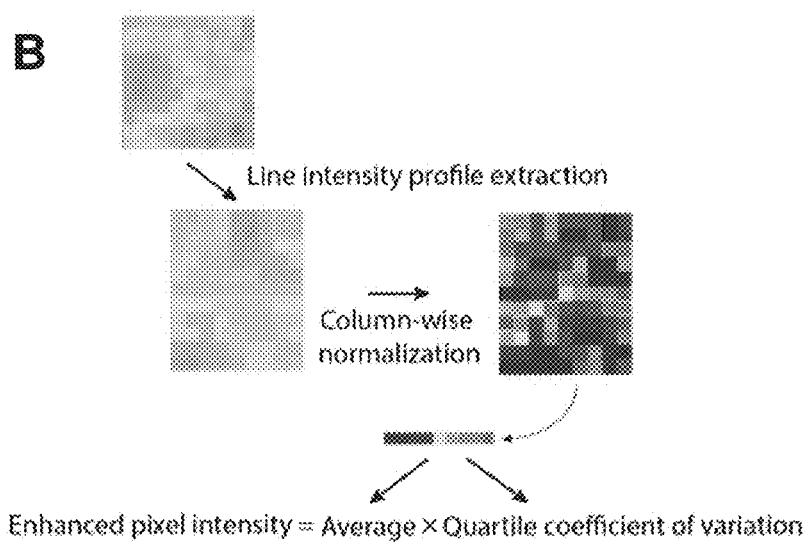
Figure 10:
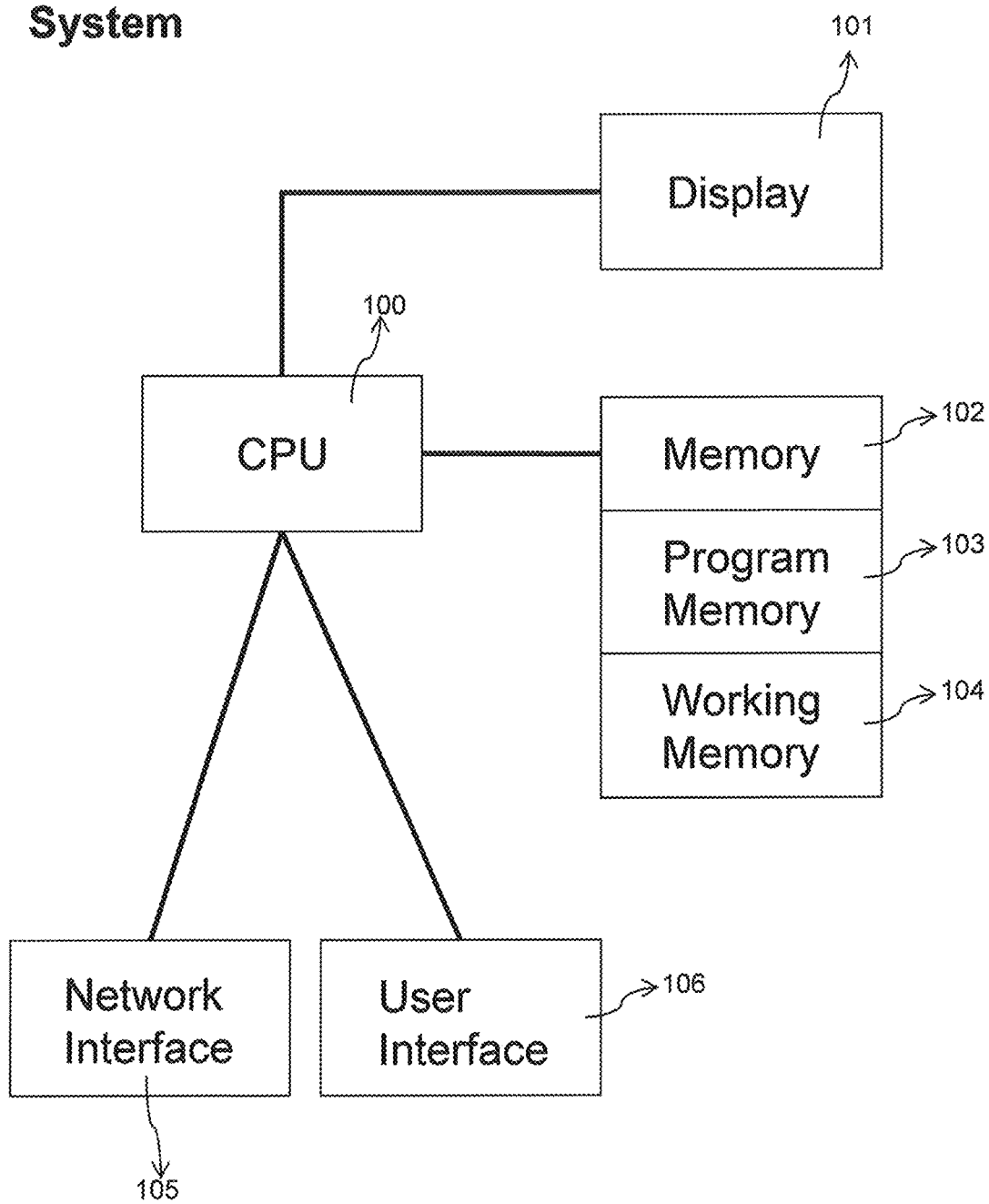
FIG. 10. Block diagram of the system in accordance with the aspects of the disclosure. CPU: Central Processing Unit ("processor") (100), Display (101), Memory (102), Program Memory (103), Working memory (104), Network interface (105), User interface (106).

Biofilms are imaged as z-stacks using the same spectral setting as described above. The voxel size is 70 nm×70 nm×150 nm to ensure sampling at the Nyquist frequency in all three spatial dimensions Image Processing for Cultured Cells The segmentation and identification pipeline is detailed in FIG. 8. Briefly, images acquired with each excitation laser are concatenated and denoised using nonlocal means Denoised images were segmented using the watershed algorithm. For each cell, an average spectrum was calculated and assigned to the corresponding barcode using a support vector machine trained on the reference spectra.

Image Processing for Biofilm Samples

Biofilm images are acquired with each excitation laser. To avoid degradation of the image quality due to stage drift, we acquire multiple volumes of the same field of view with short pixel dwell time at low signal to noise ratio, and computationally align the volumes to generate an average volume with minimal stage drift artefacts and high signal to noise ratio. For each voxel in the aligned volume, we extract the line profile in multiple directions that goes through the voxel under consideration. The structuring elements for the line profiles are parameterized by the azimuthal angle θ and polar angle φ. Each line profile is rescaled to the range [0,1]. The quartile coefficient of variation for each voxel is also calculated. To produce the pre-processed image, the neighbor profile image was pixel-wise multiplied with (1-quartile coefficient of variation image). To separate signal voxel from background voxel in the pre-processed image, a kmeans clustering algorithm with 2 clusters was used. Then a binary opening function was applied to the image to remove any residual connections between neighboring objects that have small number of connecting voxels. Any objects that are less than 10 voxels in size were removed, primarily to remove spuriously segmented objects in the background, and use binary filling functions to fill in any holes in the segmented objects. Finally, the objects were label in the resulting image, which serve as the seed image for the watershed algorithm. To generate a mask image for watershed algorithm, the natural log of the raw volume averaged along the spectral axis were taken and a kmeans clustering algorithm with 2 clusters was used to separate out cells from the background. The intensity image for the watershed algorithm is simply the raw voxel averaged along the spectral axis. (A watershed is a transformation defined on a grayscale image. The name refers metaphorically to a geological watershed, or drainage divide, which separates adjacent drainage basins. The watershed transformation treats the image it operates upon like a topographic map, with the brightness of each point representing its height, and finds the lines that run along the tops of ridges.) Finally, watershed segmentation was performed using the intensity image, seed image, and the mask image generated above.

The pre-processed image is then segmented using a k-means clustering algorithm with two clusters. The cluster of voxels with the higher intensity are designated as cell voxels, while the rest are background voxels. The segmented image was labeled and used as the watershed seed image for single cell segmentation.

Barcode Decoding

A support vector machine (SVR, sklearn.svm Python package) was trained on reference data to predict the barcode of single cells in the synthetic communities and environmental samples. Reference spectra can be obtained by simulation or through a brute force approach. The brute force approach involves the measurement of the spectra of all possible barcodes using barcoded *E. coli* cells. For a 10-bit HIPR-FISH, this requires measurement of 1023 reference spectra. To accomplish the 1023-way multiplexed experiment, reference spectra were obtained for 1023 barcodes (approximately 36 hours of imaging). Therefore, the brute force approach is tractable for HIPR-FISH with up to 10 bits. For HIPR-FISH with a greater number of bits, simulated data can be used as reference examples for the support vector machine. Here, barcodes are simulated by adding together the measured spectra of each individual fluorophore (e.g. the reference spectrum for 0000010011 is generated by adding the spectra of R1, R2, and R5). Simple summation of the individual fluorophore spectra to generate arbitrary barcodes, however, does not account for possible FRET between fluorophores. FRET can be addressed using more detailed modeling.

Example 2: Binary Barcoding Principle in Microbes

Figure 1B:
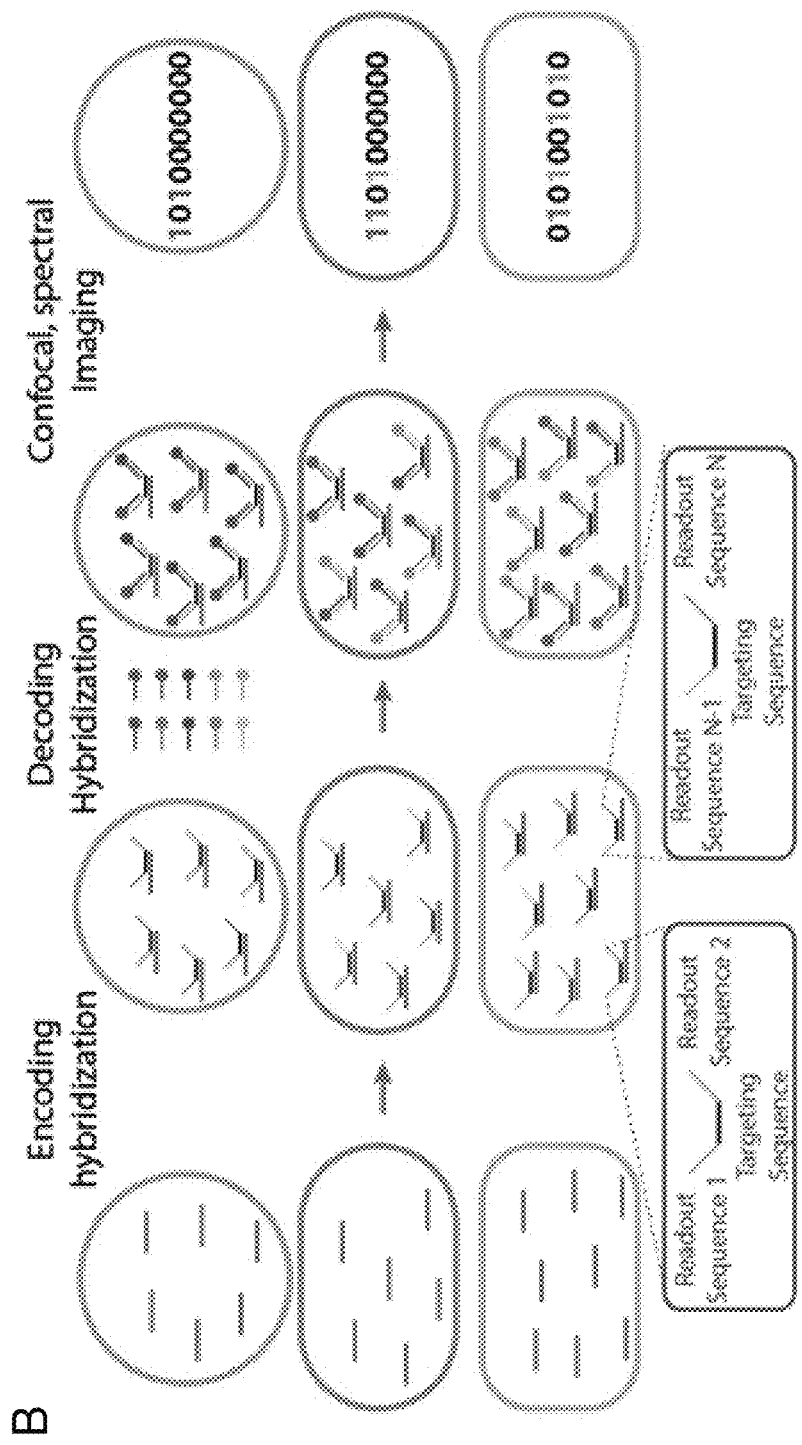
Figure 1C:
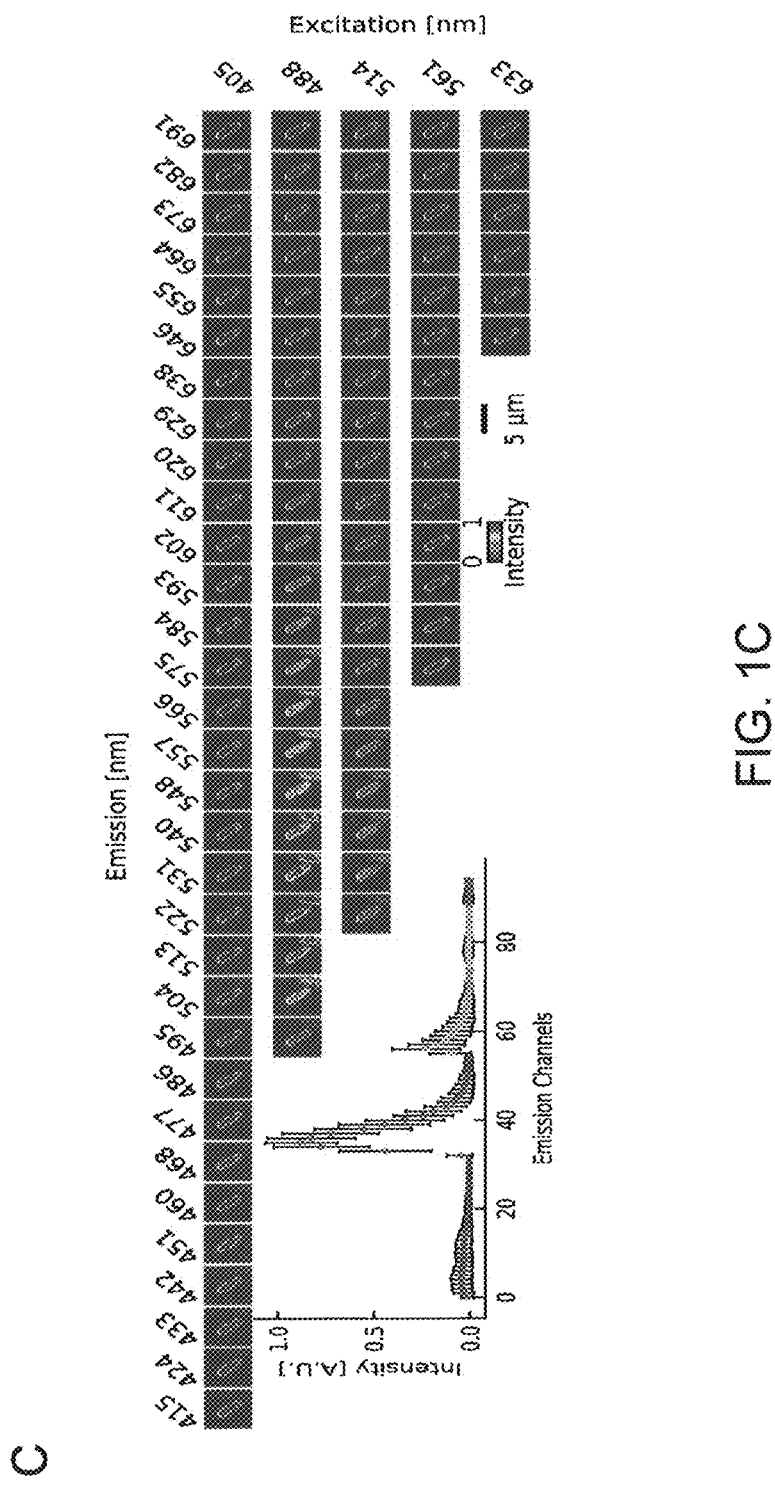
Figure 1D:
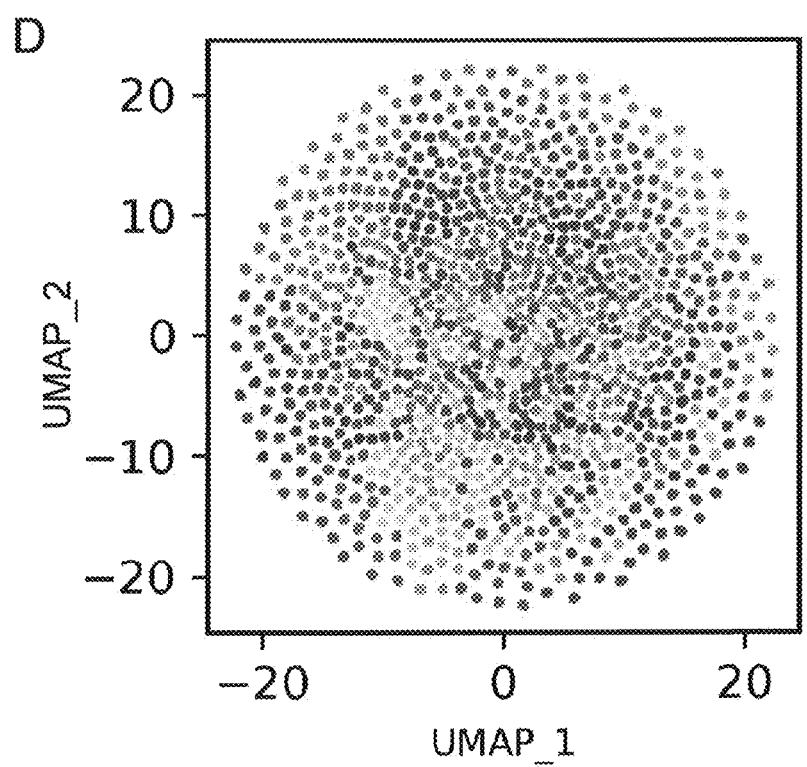

High multiplexity is achieved herein by using a binary encoding scheme to translate taxon identity to binary words (FIGS. 1A and 1B). Each taxon of microbes in a biofilm community is probed with a custom designed taxon-specific targeting sequence, flanked by a subset of n unique encoding sequences. Each taxon is assigned a unique n-bit binary word, where 1 or 0 at the $i^{th}$ bit indicates the taxon-specific targeting sequence is flanked or not flanked by the $i^{th}$ encoding sequence. A mixture of n readout probes, each complementary to one of the n encoding sequences and conjugated to a unique fluorophore, is then allowed to hybridize to their complementary encoding sequences. To decode the barcodes, we measure the spectrum of individual cells (FIG. 1C), and use a combination of support vector machine and uniform manifold approximation and projection to classify single-cell spectra against a reference database of all possible spectra (FIG. 1D). The key to our scheme lies in the abundance of ribosomes in individual microbial cells. During an experiment, a mixture of probes with the same targeting sequence but different encoding sequence can hybridize stochastically to ribosomal RNA molecules in each cell, allowing the cell to be labeled with up to n kinds of unique fluorophores. In other words, the ribosomal RNA molecules are conceptually divided into multiple groups, where each group is labeled with an oligo probe with one targeting sequence and two encoding sequences.

To generate a complex pool of species-specific FISH probes, first all 16S rRNA sequences in each database were binned by taxon. For each taxon, a consensus 16S sequence was generated, FISH probes were designed, each probe was blasted against a database containing all 16S sequences of the community, and the best probe was selected based on the blast on-target rate and taxonomic coverage. Taxon-specific probes with blast on-target rate less than 0.99 were excluded from the final probe set to avoid ambiguous encoding. Each taxon-specific probe in the final pool was conjugated to appropriate encoding sequences according to its assigned binary code. To further reduce false positive rates, the blast result of each probe was examined against the database of full length 16S sequences, and design competition probes for likely off-target binding sites. As an example, probe 923 for *Acinetobacter schindleri* in the multispecies synthetic community experiment has likely off-target binding sites on the 16S rRNA molecules in *Vibrio albensis* and *Enterococcus gallilarium*, both with one base pair mismatch. Therefore two competitor probes with sequences that are exactly complementary to the 16S rRNA molecules in *Vibrio albensis* and *Enterococcus gallilarium* were introduced. These competitor probes did not have any flanking region for readout probe hybridization, and therefore did not add any fluorescent signals during detection. Their only role was to compete with probe 923 during hybridization, so that the promiscuous probe 923 is largely excluded from binding to *Vibrio albensis* and *Enterococcus gallilarium*.

For experiments in this study, the following 10 fluorophores (R1-R10) that are reasonably separated in terms of optimal excitation wavelength and emission spectra were selected: R1: Alex488N, R2: Alex546N, R3: 6-ROXN, R4: PacificGreenN, R5: PacificBlueN, R6 Alex6ION, R7: Alex647N, R8: DyLight-510-LS, R9: Alex405N, and R10: Alex532N. See Table 2. However, in other embodiments other fluorophores, such as Hydroxycoumarin, methoxycoumarin, Cy2, FAM, Flourescein FITC, Alexa 430, R-phycoerythrin (PE), Tamara, Cy3.5 581, Rox, Alexa fluor 568, Red 613, Texas Red, Alexa fluor 594, Alexa fluor 633, Alexa fluor 660, Alexa fluor 680, Cy5, Cy 5.5, Cy 7, and Allophycocyanin, may be used.

To compensate for differences in emission strength of fluorophores with the same optimal excitation laser, the inventors diluted R2 with an equal concentration of unlabeled oligo, and labeled R3, R8, and R10 oligos with fluorophores on both the 3' and the 5' end. See Table 1.

For each field of view, spectral images were acquired sequentially using different excitation lasers. Spectral images were then segmented using a custom algorithm. For each cell, the spectra were averaged across all the pixels belonging to that cell and use a two-stage classification approach. To train the classifier, first uniform manifold approximation and projection (UMAP) was used to reduce the high dimensional spectra into two dimensions. A custom excitation-channel-wise cosine distance kernel was used in UMAP to achieve clean separation between all barcodes. Spectra for each barcode clusters were tightly in the two-dimensional representation. Then a support vector machine was trained using the two-dimensional representation of all the reference spectra. During prediction, a new spectrum was reduced to two dimensions using the same UMAP transformation that were trained on the reference dataset and send the two-dimensional representation to the SVM classifier for prediction.

Example 3: Binary Barcoding in an *E. coli* Community

Figure 2A:
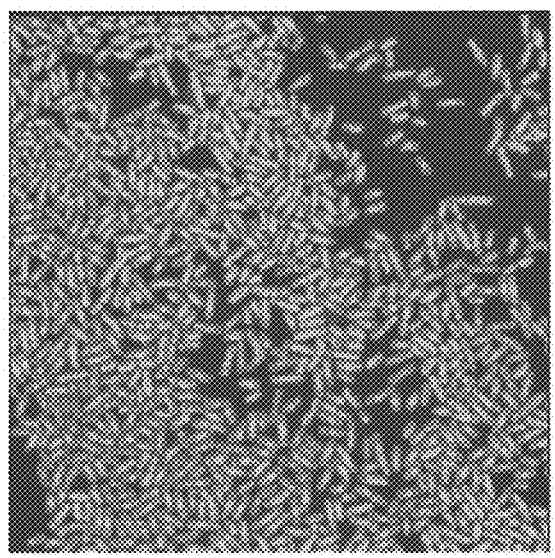
FIGS. 2A-2D. (A) A typical field of view of *E. coli* cells. The raw image has been averaged over the spectral dimension to generate a 2D representation. (B) Single cell segmentation of the field of view in (a). (C) Histogram of the relative abundance of an equal-concentration mixture of all 1023 species of barcoded *E. coli* cells. (D) Correlation of measured abundance and input abundance in K col synthetic communities. Each community consists of 127 to 128 species of barcoded *E. coli* cells at varying concentrations.
Figure 2B:
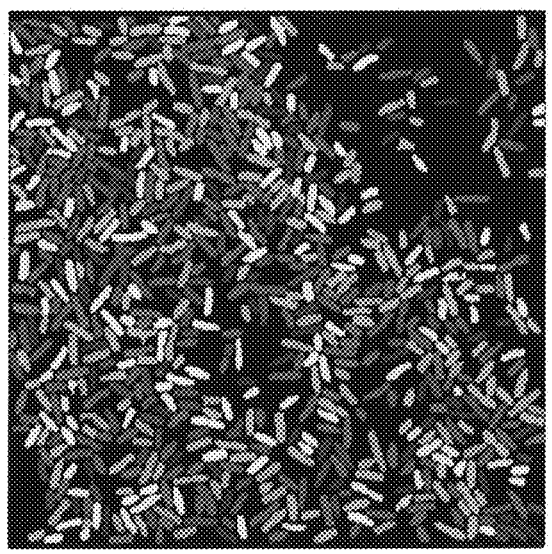
Figure 2C:
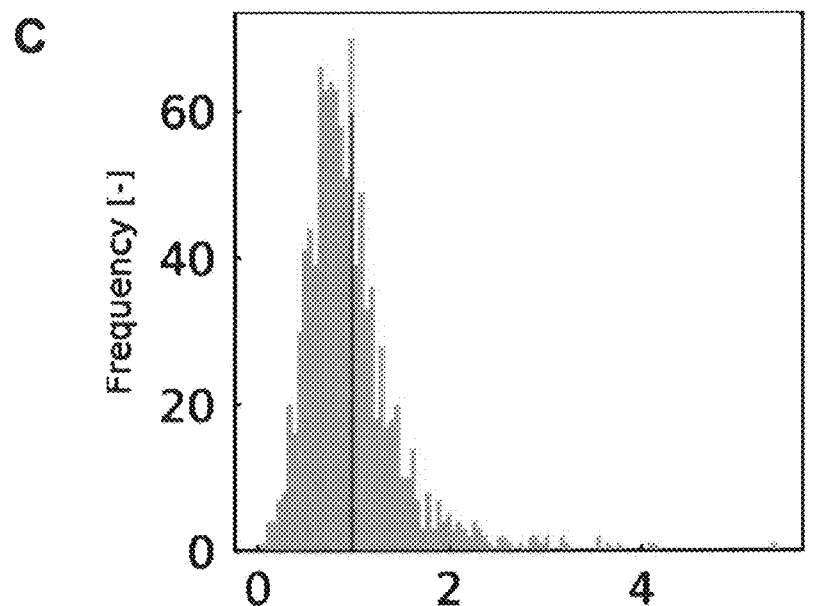
Figure 2D:
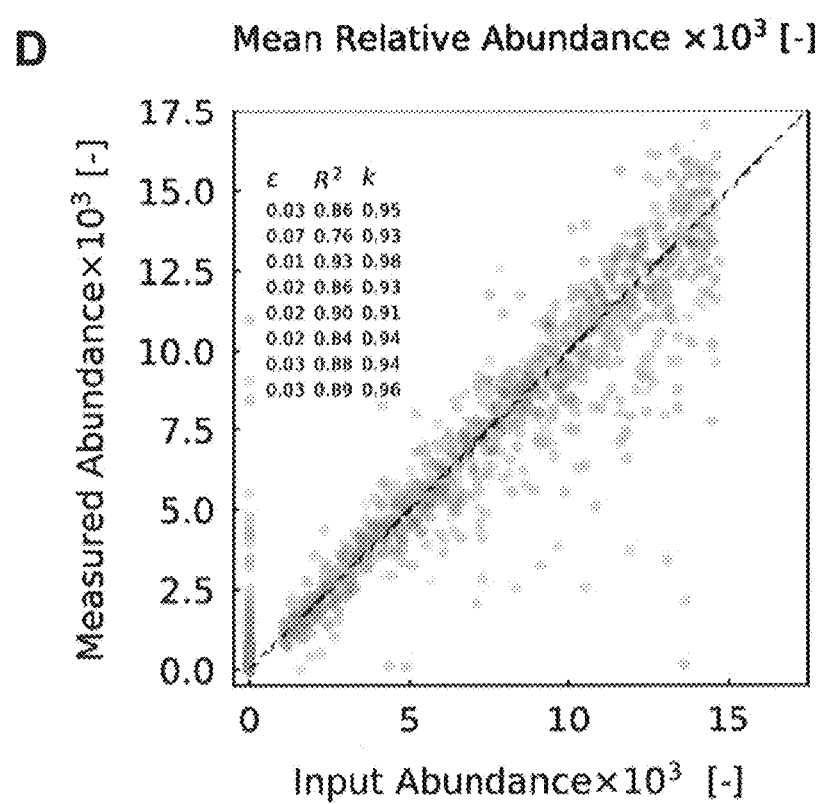

To demonstrate the principle and feasibility of HiPR-FISH, 1023 aliquots of *E. coli* cells were encoded using a 10-bit encoding scheme. Each aliquot of *E. coli* cell is hybridized with a unique encoding barcode. For each aliquot, spectral images were recorded using five excitation lasers and concatenated them into one image. Raw images were averaged along the spectral axis (FIG. 2A) and used for single cell segmentation mask (FIG. 2B). Concatenated spectra measured using the raw images and the segmentation masks were used to generate a reference database of single-cell spectra for each barcode. Then, all *E. coli* aliquots were mixed at equal volume and the resulting mixture was imaged. All 1023 barcodes in the resulting mixture were detected, and all barcodes had similar relative abundance in the mixture (FIG. 2C). The 1023 aliquots were also randomly divided into 8 groups, where each group included 127 or 128 barcodes, were mixed together barcodes in the same group at varying concentration, and were measured the relative abundance in the mixtures. Measured relative abundances strongly correlated with input relative abundances (FIG. 2D). Within each group, there were only 127 or 128 barcodes that should be detected, 50 fields of view were measured for each group. In total, 35,000 to 40,000 single cell spectra were measured per group. Any assignment to barcodes that does not belong to the group is a clear mis-assignment error and can serve as a measure for the accuracy of the classification scheme. To characterize the accuracy of the two-stage classification scheme, gross error rate was defined as the fraction of all barcodes that does not belong to the list of barcodes that were in each group. Using images of the group mixtures, it was found that barcode mis-assignment is rare, with gross error rates ranging from 0.8% to 6.7%.

Example 4: Binary Barcoding in a Multispecies Community

To demonstrate the principle of HiPR-FISH, a mock community consisting of 11 species of bacteria was probed and imaged. The probes were designed using the custom algorithm described above.

Figure 3A:
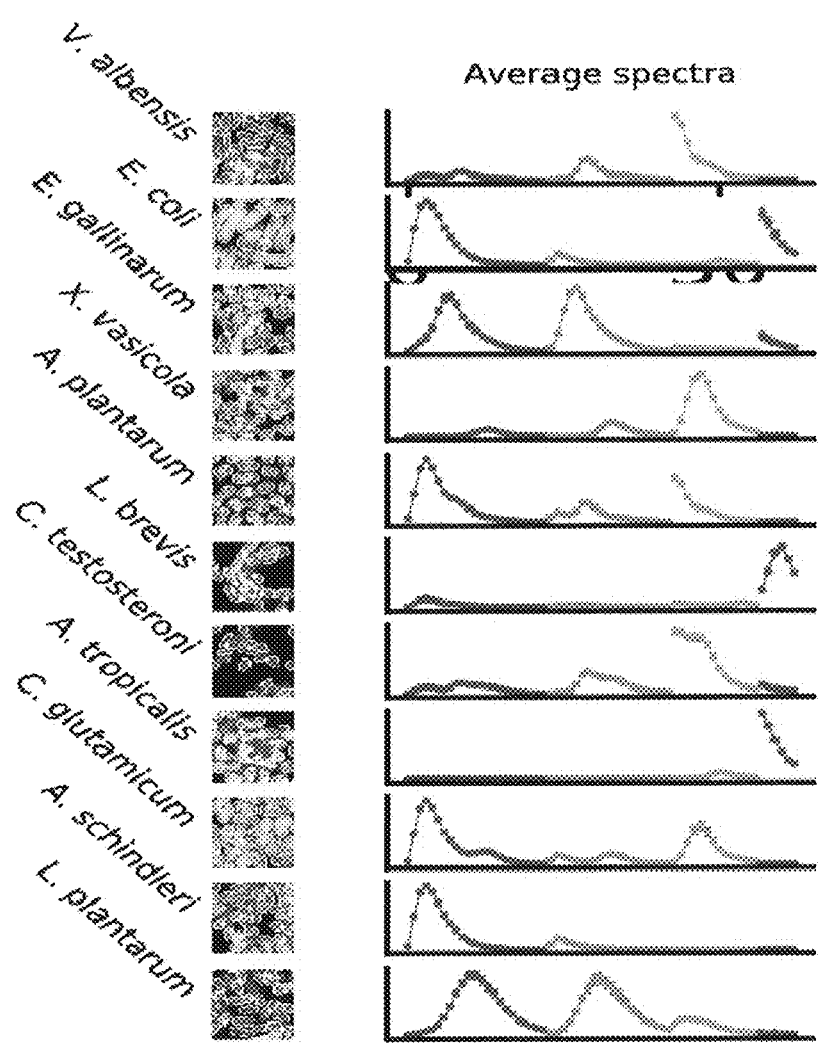
FIGS. 3A-3B. (A) Representative images and average spectrum of each of the 11 species in the synthetic community. (B) Misidentification rate for each species in the synthetic community. Blue data points indicate that there were actual misidentified objects in the field of view. Orange data points indicate that all objects in the image were corrected identified, and the misidentification rate is calculated as an upper limit of the inverse of number of cells in the field of view.
Figure 3B:
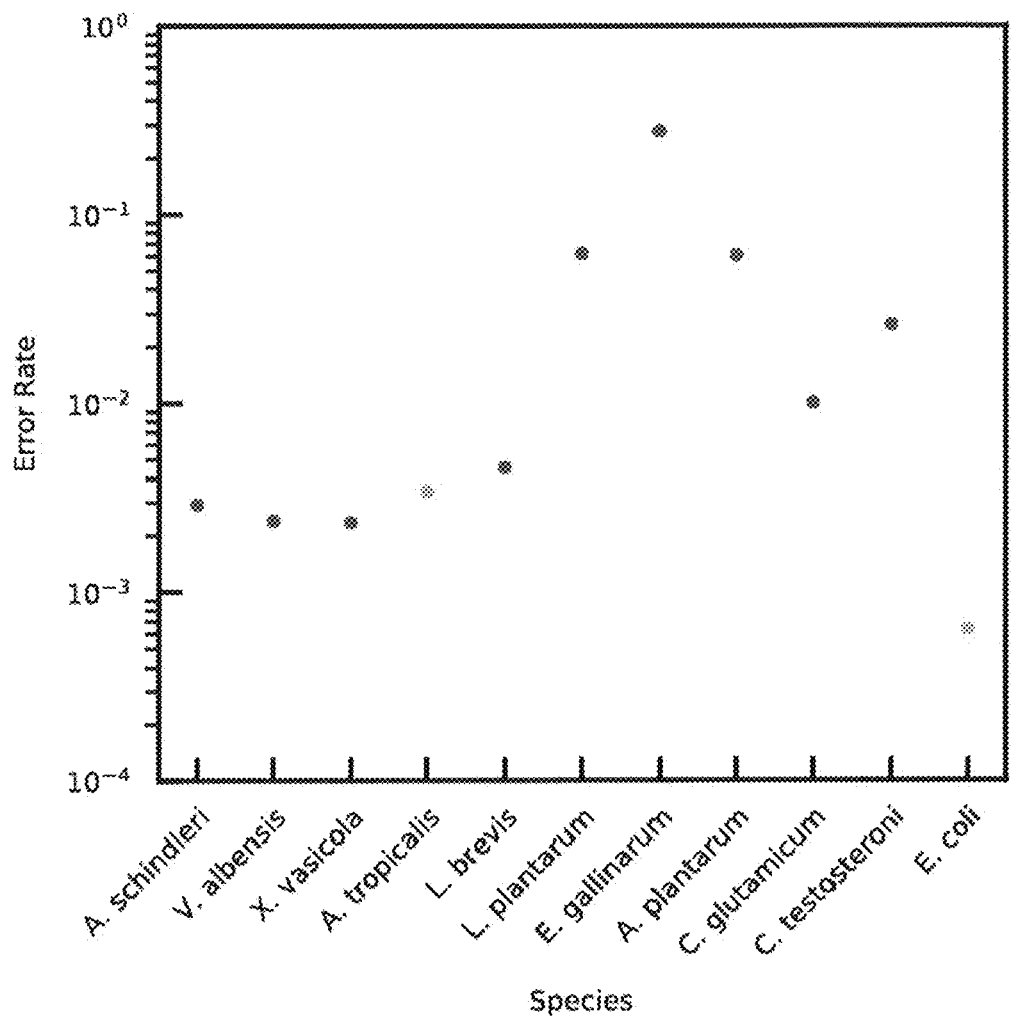

To evaluate the specificity of the custom-designed species-specific probes, the entire probe set was hybridized to pure cultures of each species in the synthetic community, spectral images were recorded for each probe set-species combination, and single-cell spectra were classified (FIG. 3A). There was a strong correlation between assigned barcode and measured barcode, with low misidentification rate (FIG. 3B). Overall, it was demonstrated that one can achieve species-specific detection and flexible binary barcode encoding using HiPR-FISH in the 11-species synthetic community.

Example 5: Synthetic Communities as Model Systems to Characterize HIPR-FISH

Figures 6A, 6B, 6C:
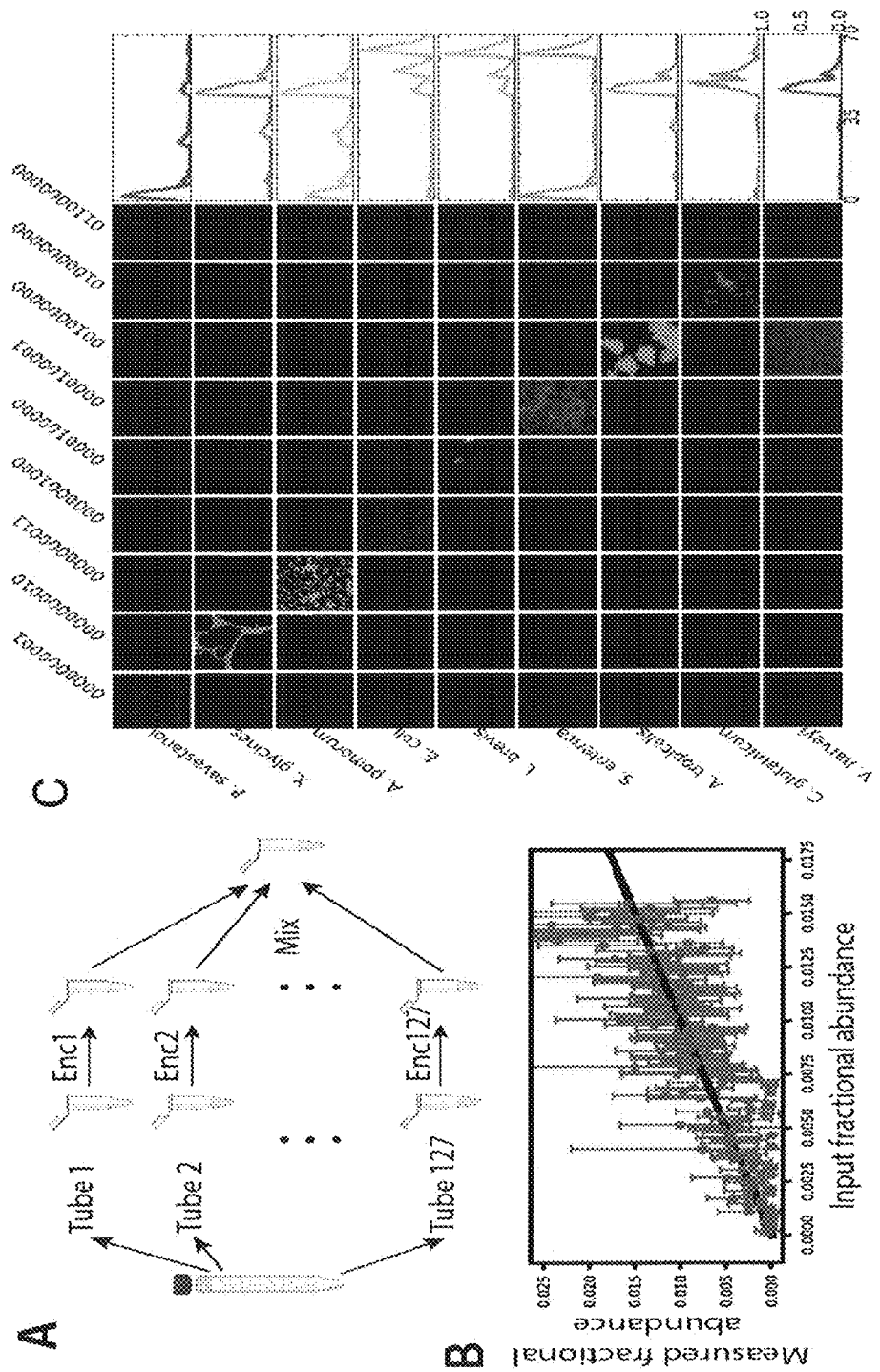
FIGS. 6A-6C. Synthetic bacterial communities to model and characterize SRM. (A) Procedure for making a synthetic 127-plex *E. coli* mixture. (B) Comparison of measured and expected synthetic *E. coli* abundance. (C) Barcode (n-bit binary code) decoding for a panel of nine distinct, cultured microbial species. 8/9 samples have been identified successfully using the disclosed system.
Figures 7A, 7B, 7C, 7D:
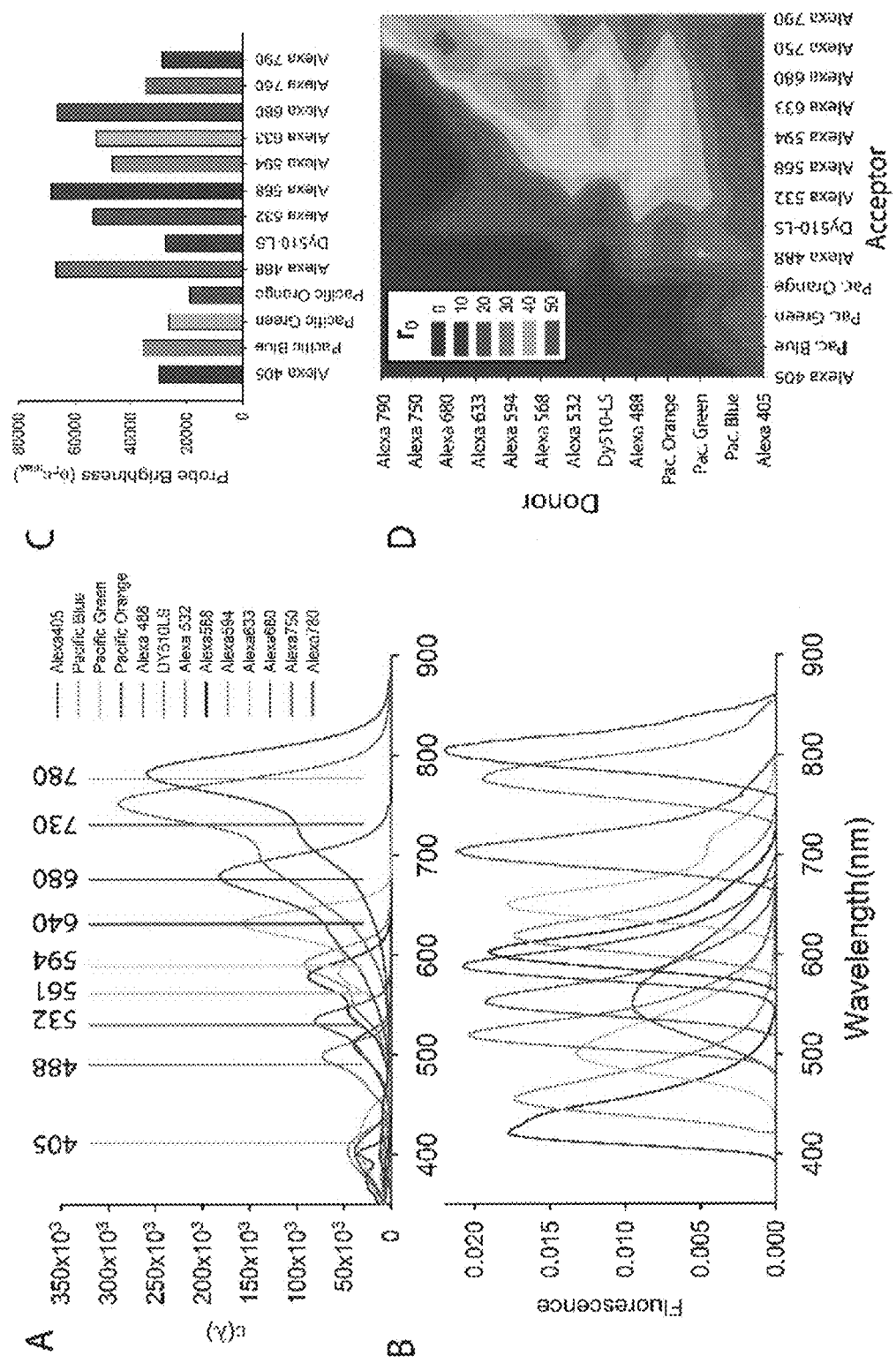
FIGS. 7A-7D. Fluorophore selection. (A) Absorption spectra of the dyes and laser lines. (B) Emission spectra (data normalized so that area under the curve is unity). (C) Brightness ($\phi F \epsilon_{max}$) distribution of the dye set. (D) FRET $r_o$ value matrix for the dye set. The $r_o$ value is the distance between dyes pairs where the FRET efficiency is 50%; to identify 16S rRNA dye pairs with the lowest $r_o$ values to minimize artifacts from energy transfer. $r_o$ values were calculated form the overlap intervals and donor quantum yields assuming $\kappa^2=2/3$ and $n=1.36$. Based on the values in the matrix, optimal probes pairs and optical filters were selected. In addition, dichroics were selected based on these dye pairs.

To characterize the performance of HIPR-FISH, and to trouble shoot the technology, two distinct model systems were used. First, a synthetic mixture of *E. coli* tagged with different n-bit barcodes was employed (FIGS. 6A-6B). This model system tests the ability to spectrally resolve n-bit barcodes in bacterial cells, and accounts for potential cell-to-cell variability in hybridization efficiency, and Farster Resonance Energy Transfer (FRET) between fluorophores that may affect emission spectra. In a pilot experiment, a 127-plex synthetic community was created, comprised of 127 *E. coli* cultures, tagged with 127 different barcodes and mixed in varying quantities. FIG. 6B shows excellent agreement between the measured and expected abundance of synthetic *E. coli* species.

Second, a multi-species synthetic community is generated, by culturing a panel of distinct bacterial species. This model system tests both the robustness of the probe-design and the ability of HIPR-FISH to probe both gram positive and gram negative bacterial strains. A nine-species community was prepared in a proof-of-principle study. FIG. 6C shows robust identification of 8/9 species. Spectral overlap between fluorophores used in an earlier version of HIPR-FISH, led to misidentification of *V. harveyi*. Based on this observation, the fluorophore set used in HIPR-FISH was optimized, avoiding spectral overlap (FIG. 1C, and FIGS. 7A-7D).

Example 6: Spatial Organization in Environmental Microbiomes

To demonstrate the feasibility of HiPR-FISH in environmental biofilm samples, HiPR-FISH was applied to human oral plaque samples and mouse gut microbiome samples. For human oral plaque experiments, a set of probes was designed at the genus level using PacBio sequencing data from a healthy volunteer sample, targeting 54 genera in total. For mouse gut microbiome experiments, a set of probes was designed at the genus level using PacBio sequencing data from a healthy control mouse stool sample, targeting 36 genera in total.

Figure 4A:
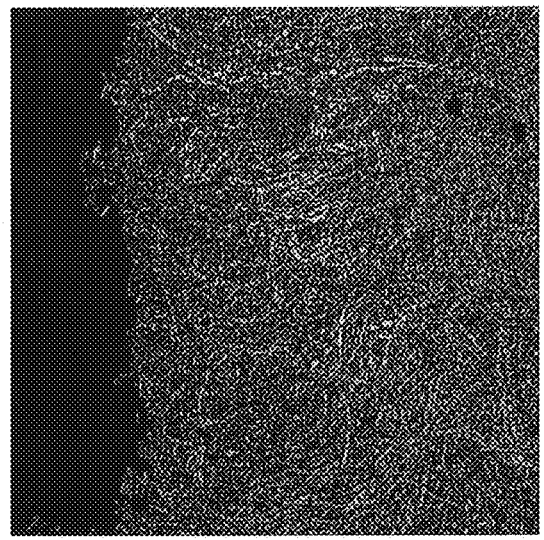
FIGS. 4A-4D. (A) A segmented and identified image of human oral plaque biofilms. (B) A segmented and identified image of healthy mouse gut microbiome. (C) Spatial association network measured using the single cell segmented and identified image in the mouse gut microbiome. (D) Frobenius distance between adjacency matrix of the spatial association network between mouse under different antibiotics treatments.
Figure 4B:
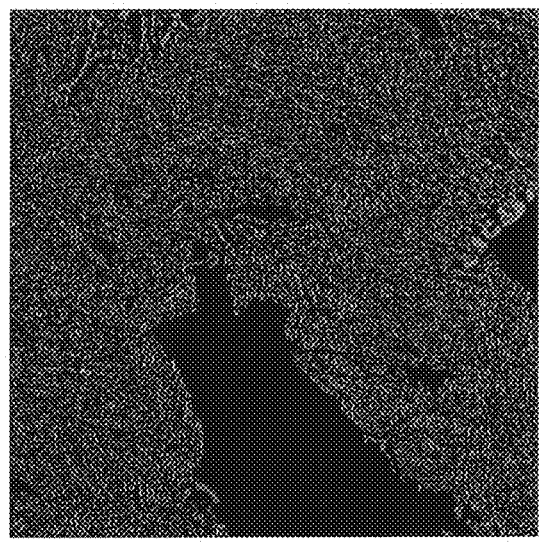
Figure 4C:
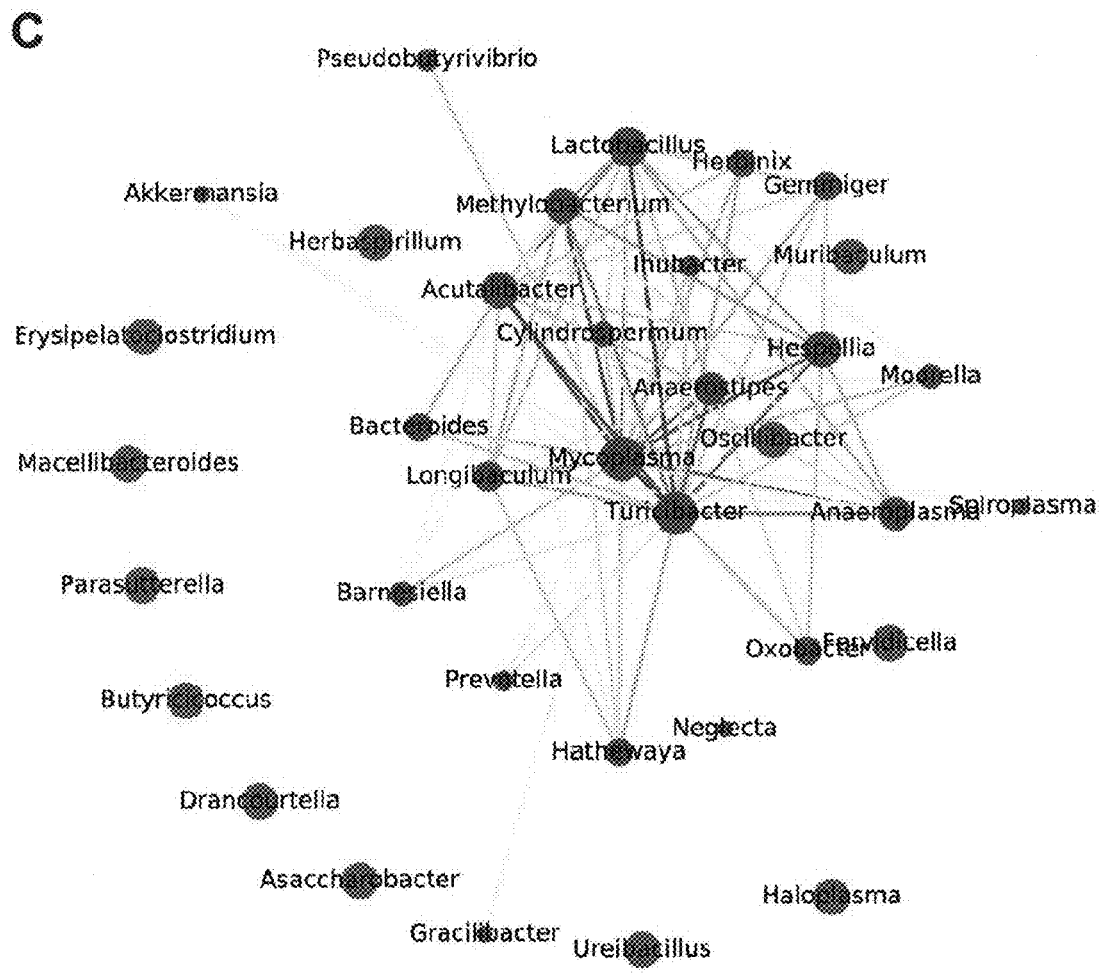
Figure 4D:
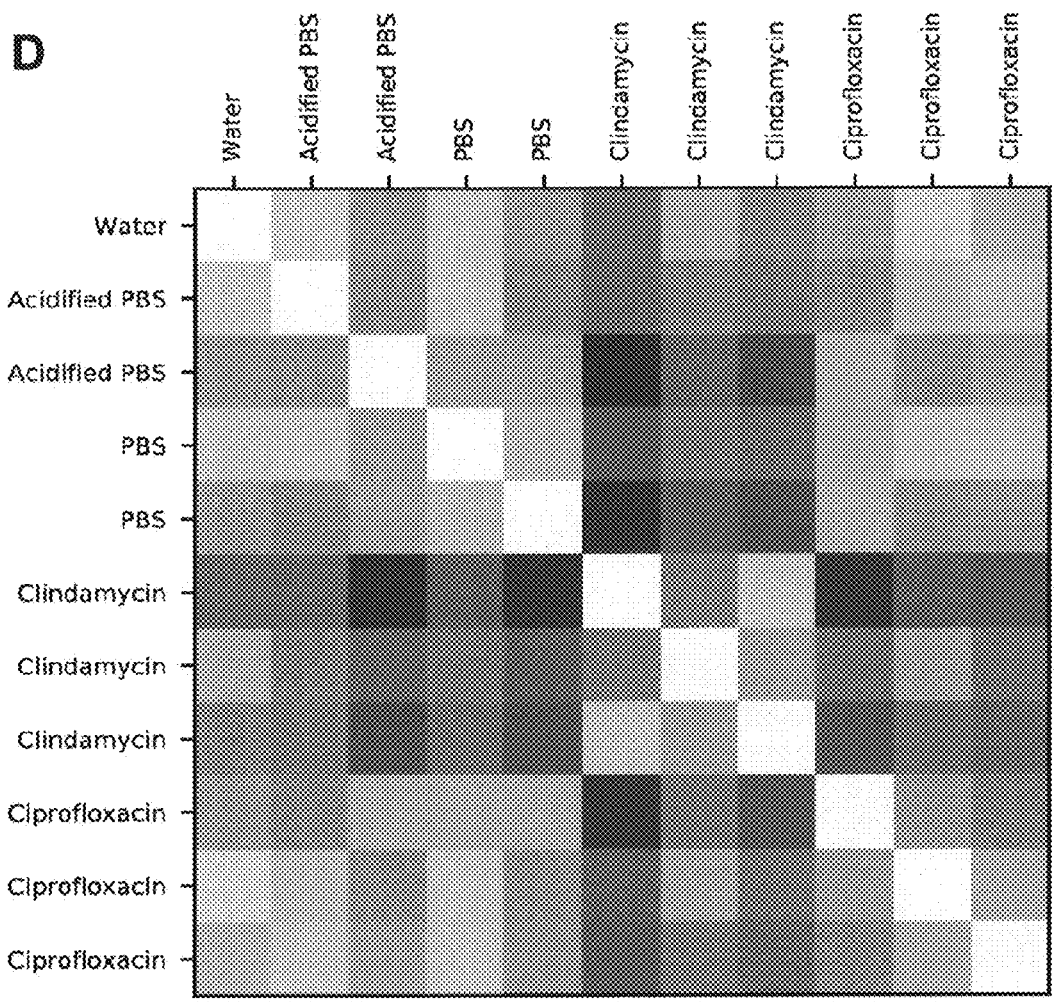

Analyzing biofilm images at the single cell level requires robust image segmentation algorithms. Watershed algorithm, the primary workhorse for segmentation tasks, generally performs very well at segmentation tasks, if the initial seed image is accurate. The major challenge in segmenting densely packed microbes can be therefore transformed to the task of finding a seed image that is closest to the ground truth image. Existing approaches for identifying local intensity maximum often require user-provided parameters that measures the average distance between local intensity peaks and assumptions about morphologies of the objects to be segmented. For biofilm samples containing microbes with diverse shapes, sizes, and ribosome density, these approaches that assumes an average ensemble property will either under- or over-segment the image volume. In principle, over-segmented volumes can be reduced using methods based on graph theory. However, such graph reduction scheme requires even more sophisticated decision trees to decide which segmented objects should belong to the same cell. To circumvent these challenges in existing algorithms, an algorithm that can reduce the global dynamic range and enhance edge contrast was developed, which are crucial for properly segmenting densely packed cells with varying ribosomal density. The local context of each pixel can provide additional information for deciding whether a given pixel or voxel should belong to a cell or to the background. For each voxel, we extract the line profile in multiple directions that goes through the voxel under consideration. The structuring elements for the line profiles are parameterized by the azimuthal angle θ and polar angle φ. Each line profile is rescaled to the range [0,1]. After these transformations, the value of the voxel of interest along each line essentially provides a measure of the intensity of the original voxel relative to its neighboring voxels along the direction of the line. Intuitively, a voxel at the center of a cell with have values close to 1, independent of the direction of the line structuring elements, while a voxel at the edge of a cell or in between two closely packed cells will be bright along some directions, and dark along others. In addition, voxels at the center of cells will have values close to 1, regardless of the actual measured intensity in the raw image. To further delineate voxels at the centers of cells and voxels along edges between cells, the quartile coefficient of variation was calculated for each voxel. Voxels near the center of cells or in the background will tend to have low quartile coefficient of variation, as most voxels around the voxel of interest will either be mostly bright (for a voxel near the center of a cell) or dark (for a voxel in the background). Finally, we pixel-wise multiply the neighbor profile image with (1-quartile coefficient of variation image) to produce the pre-processed image, which exhibit low global dynamic range and sharp boundaries between closely packed cells. Using a custom approach, biofilm images were segmented from the human oral plaque microbiome (FIG. 4A) and the mouse gut microbiome (FIG. 4B). The digital representation of segmented biofilm images allows to generate single-cell adjacency matrices and directly visualize the spatial association network in complex environmental microbiomes (FIG. 4C).

Example 7: Encoding Probe

In a non-limiting example, one non-limiting example of an encoding probe has the sequence SEQ ID NO: 11. See FIG. 1E. The exemplified encoding probe is designed specifically target (i.e., is substantially complementary to) unique consensus site at the *Lactobacillus plantarum* (NCBI Taxonomy ID: 1590) 16S RNA. In this example, *Lactobacillus plantarum* has been pre-assigned the 10-bit binary code of "0000000001."

Each digit in a unique binary code represents whether a readout probe and the fluorophore corresponding to that readout probe are present for the selected species. The digits in the binary code correspond to Readout probe 1 (R1) through Readout probe 1 (R10) as seen in FIG. 1F. The fluorophores that correspond to R1 through R10 can be determined arbitrarily. In some embodiments, R1 corresponds to an Alexa 488 fluorophore, R2 corresponds to an Alexa 546 fluorophore, R3 corresponds to a 6-ROX (6-Carboxy-X-Rhodamine, or Rhodamine Red X) fluorophore, R4 corresponds to a PacificGreen fluorophore, R5 corresponds to a PacificBlue fluorophore, R6 corresponds to an Alexa 610 fluorophore, R7 corresponds to an Alexa 647 fluorophore, R8 corresponds to a DyLight-510-LS fluorophore, R9 corresponds to an Alexa 405 fluorophore, and R10 corresponds to an Alex532 fluorophore. See Table 1. However, the matching of the Readout probes and the labels may be changed. In addition, the fluorophores are not limited to the ones listed in this Example, and different fluorophores may be substituted for the ones used herein. For instance, a fluorophore selected from Hydroxycoumarin, methoxycoumarin, Cy2, FAM, Flourescein FITC, Alexa 430, R-phycoerythrin (PE), Tamara, Cy3.5 581, Rox, Alexa fluor 568. Red 613, Texas Red, Alexa fluor 594, Alexa fluor 633, Alexa fluor 660, Alexa fluor 680, Cy5, Cy 5.5, Cy 7, and Allophycocyanin can be substituted with the fluorophores already discussed above. In some embodiments, other fluorophores that emit at the infrared or near-infrared spectrum may also be used.

In this instance, the assigned 10-bit binary code "0000000001" indicates that the species *Lactobacillus plantarum* is matched to a single readout probe (Readout probe 1—R1) which is in this case labeled with Alex488N.

In another non-limiting example, a second bacterial species, *Lactobacillus brevis* (NCBI Taxonomy ID: 1580), was assigned the binary code "0000000010" which means that the readout sequence R2 (in this instance conjugated to Alexa 546) is used to represent this bacterial species. (See SEQ ID NO: 12 which provides an example sequence of an encoding probe targeting *Lactobacillus brevis* with the 10-bit binary code 0000000010.)

In another non-limiting example, a third bacterial species, *Xanthomonas vasicola* (NCBI Taxonomy ID: 56459), was assigned the binary code "0000000011" which means that the readout sequences R1 (Conjugated to Alexa 488), and R2 (conjugated to Alexa 546 in this example) are used to represent this bacterial species. (See SEQ ID NO: 13 which provides an example sequence of an encoding probe targeting *Xanthomonas vasicola* with the 10-bit binary code 0000000011).

Similarly, in a non-limiting example, a taxon which is assigned a binary code of "1111111111" will have encoding probes that comprise all the readout sequences R1-R10 (in at least 5 encoding probe constructs). Using the binary encoding strategy defined herein, the skilled artisan can design encoding probes for multiple bacterial species.

FIG. 5 (top) demonstrates an example orientation of elements in an encoding probe: Forward primer. Readout Sequence 1, 3-nucleotide spacer, Targeting Sequence, 3-nucleotide spacer, Readout Sequence 2, and Reverse Primer.

Figure 1E:
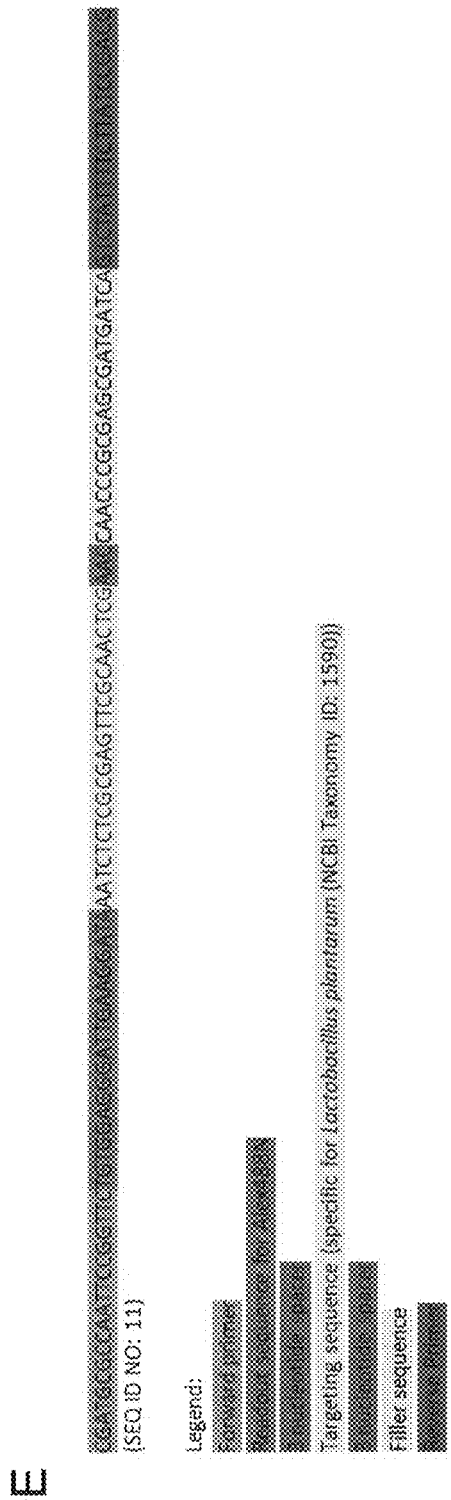
Figure 1F:
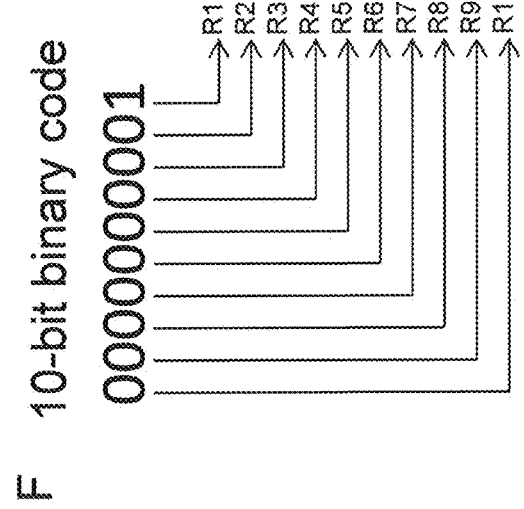

In the specific example of FIG. 1E (SEQ ID NO: 11), it is noted that Readout Sequence 2 is substituted with a random filler sequence, because, in this example, the target species *Lactobacillus plantarum* was assigned only a single readout sequence. The random filler sequence ensures that all encoding probes are of roughly the same size, which improves efficiency in probe synthesis.

Example 8

The inventors have developed a flexible, cost-effective, and highly multiplexed imaging method to survey the micron-scale biogeography of environmental microbial communities. HiPR-FISH leverages the strengths of sequencing and FISH strategies and offers a versatile platform to probe the spatial distribution of microbial species within communities in a highly-multiplexed fashion. The probe design algorithm in HiPR-FISH allows the design of high-quality FISH probes with low promiscuity and high taxonomic coverage.

In addition to the high multiplexity and taxonomic resolution, HiPR-FISH offers significant flexibility to survey the biogeography of microbial communities with substantially different taxonomic composition. The targeting sequences in the encoding probe construct can be substituted at will, allowing researchers to design probe sets for communities with different composition without incurring significant financial burden that are typically associated with existing FISH strategies. High resolution phylogenetic mapping of microbial communities can provide previously inaccessible insights into the ecology and function of natural microbial biofilm communities.

HiPR-FISH takes advantage of a binary encoding scheme to label microbes of different species, which allows detection of more than 1000 species with just 10 fluorophores. Compared to existing FISH approaches, HiPR-FISH enables imaging biofilm spatial structure at high taxonomic level (e.g. species) without sacrificing the number of detectable taxa in a single experiment. In addition, the two-step hybridization approach and the probe construct provide strong flexibility to investigate new microbial communities without incurring substantial overhead cost in probe synthesis. Researchers interested in studying a new biofilm system can simply design new targeting sequences and use the same set of encoding sequences.

The custom approach disclosed herein allows automatic segmentation of environmental biofilm images at the single cell level. Segmented images can enable many downstream quantitative analyses of microbial community spatial structure.

Imaging of a 11-species synthetic community demonstrates that HiPR-FISH can identify cells in different species with high fidelity. Application of HiPR-FISH to human plaque samples revealed the genus-level spatial organization of human oral microbial communities, and enabled identification of structural changes in mouse gut microbial spatial association network under antibiotics treatment.

HiPR-FISH is robust and flexible. Bacteria express 16S rRNA at high copy number (100s-1000s of copies). This makes HiPR-FISH inherently robust, i.e. unlike related techniques for mammalian spatial transcriptomics, HiPR-FISH does not require single molecule imaging resolution. Because 16S rRNA are distributed relatively uniformly across bacterial cells, the 3D spatial image resolution required for HiPR-FISH (~0.5 µm) is readily achieved with standard fluorescent confocal imaging. The high copy number of 16S transcripts in bacteria provides further flexibility in probe sequence design: In HiPR-FISH, the number of flanking sequences per probe sequence is limited to two, and n-bit encoding with n>2 is achieved with a mixture of probe sequences targeting the same species. For example, 10-bit HiPR-FISH is achieved with a mixture of five probe sequences targeting the same 16S sequence, each flanked with two unique encoding sequences.

HiPR-FISH is inexpensive. The encoding probe sequences are not modified with fluorophores and can therefore be synthesized using inexpensive array technology (cost per oligo ~$0.1). The readout/decoding probes are modified with fluorophores, and are expensive ($100-200 per oligo), but crucially, only n unique readout probes are needed, and readout probes can be re-used across experiments targeting different systems.

HiPR-FISH enables a greater than 100× improvement in multiplexity over existing approaches. In HIPR-FISH, the number of unique binary codes grows exponentially with the number of bits. The data presented herein demonstrates the feasibility of 10-bit HiPR-FISH on a commercial microscope system, enabling identification of $2^{10}-1$ or 1023 unique microbial species in a specimen. This translates to a 10-100× improvement over existing approaches.

HiPR-FISH is fast and therefore compatible with imaging of a large surface area. The multiplexity in HiPR-FISH is achieved with multi-color imaging, enabling spatial mapping of the microbiome from a single confocal imaging scan. Related techniques for mammalian transcriptomics require sequential hybridization, and are therefore much slower. A fast acquisition speed is critical to achieve microbiome mapping over multi microscope fields of views.

The present approach provides a comprehensive framework for measuring microbial spatial organization at the single cell level. The phylogenetic measurements can provide clues to potential metabolic interactions between microbial taxa, which can be especially useful for yet-uncultivable microbes from the environment. Single cell segmentation of environmental biofilm can generate quantitative insights into microbial community assembly from a physical perspective and become a rich resource for testing soft matter theories that describe microbial community assembly rules.

What is claimed is:

1. A method comprising:
   providing a list of taxa of microorganisms, wherein each taxon in the list is assigned a unique n-bit binary code selected from a plurality of unique n-bit binary codes, and wherein n is an integer equal or greater than 10;
   providing a set of n number of decoding probes, wherein each decoding probe
      corresponds to a digit in the plurality of unique n-bit binary codes,
      is conjugated with a label that provides a detectable signal, wherein the labels on the decoding probes are different from each other, and
      is substantially complementary to a readout sequence selected from a set of n number of readout sequences;
   providing a set of encoding probes, wherein the set of encoding probes includes a plurality of subsets of encoding probes, wherein
      each encoding probe comprises a targeting sequence and one or more readout sequences,
      the encoding probes within each subset comprise a targeting sequence that is specific to a taxon in the list of taxa of microorganisms and is different from a targeting sequence of the encoding probes of another subset, and
      the readout sequences in the encoding probes within a subset are selected from the set of n number of readout sequences based on the unique n-bit binary code assigned to the taxon which the targeting sequence of the subset is specific to;
   providing a sample suspected of comprising one or more of the taxa of microorganisms;
   contacting the sample with the set of encoding probes to permit hybridization of the targeting sequences to the corresponding taxa of microorganisms present in the sample;
   subsequently contacting the sample with the set of decoding probes to permit hybridization of one or more decoding probes to the readout sequences in encoding probes that are bound to the sample;
   detecting the decoding probes that are bound to the sample after a single round of two-step hybridization with the encoding probes and decoding probes;
   determining the unique binary codes based on the detected decoding probes; and
   identifying the taxa of microorganisms present in the sample based on the determined unique binary codes.

2. The method of claim 1, wherein the targeting sequence for a subset of encoding probes is substantially complementary to a consensus 16S ribosomal sequence specific to a taxon.

3. The method of claim 1, wherein the encoding probes within each subset comprise a plurality of targeting sequences, wherein the plurality of targeting sequences are specific to the same taxon.

4. The method of claim 1, wherein the list of taxa of microorganisms is selected from a list of phyla, a list of classes, a list of orders, a list of families, a list of genera, or a list of species.

5. The method of claim 1, wherein the label is a fluorophore.

6. The method of claim 5, wherein the fluorophore is selected from the group consisting of Alexa 405, Pacific Blue, Pacific Green, Alexa 488, Alexa 532, Alexa 546, Rhodamine Red X, Alexa 610, Alexa 647, DyLight-510-LS, Hydroxycoumarin, methoxycoumarin, Cy2, FAM, Florescein FITC, Alexa 430, R-phycoerythrin (PE), Tamara, Cy3.5 581, Rox, Alexa fluor 568, Red 613, Texas Red, Alexa fluor 594, Alexa fluor 633, Alexa fluor 660, Alexa fluor 680, Cy5, Cy 5.5, Cy 7, and Allophycocyanin.

7. The method of claim 1, wherein the detecting is achieved by a microscope.

8. The method of claim 1, wherein the determining is achieved by a support vector machine.

9. The method of claim 1, wherein the sample is selected from an environmental sample or a biological sample.

10. The method of claim 9, wherein the biological sample is selected from the group consisting of bronchoalveolar lavage fluid (BAL), blood, serum, plasma, urine, cerebrospinal fluid, pleural fluid, synovial fluid, peritoneal fluid, amniotic fluid, gastric fluid, lymph fluid, interstitial fluid, tissue homogenate, a tumor, cell extracts, saliva, sputum, stool, physiological secretions, tears, mucus, sweat, milk, semen, seminal fluid, and vaginal secretions.

11. The method of claim 1, wherein the sample is a solid sample or a liquid sample.

12. The method of claim 1, wherein the sample is washed after each hybridization with encoding probes and decoding probes.

13. The method of claim 1, wherein each decoding probe comprises at least 10 nucleotides.

14. The method of claim 1, wherein each targeting sequence comprises at least 15 nucleotides.

* * * * *